US012559461B2

(12) United States Patent
Melander et al.

(10) Patent No.: US 12,559,461 B2
(45) Date of Patent: Feb. 24, 2026

(54) ANTIBIOTIC ADJUVANT COMPOUNDS

(71) Applicant: UNIVERSITY OF NOTRE DAME DU LAC, South Bend, IN (US)

(72) Inventors: Christian Melander, South Bend, IN (US); Veronica Hubble, South Bend, IN (US)

(73) Assignee: UNIVERSITY OF NOTRE DAME DU LAC, South Bend, IN (US)

( * ) Notice: Subject to any disclaimer, the term of this patent is extended or adjusted under 35 U.S.C. 154(b) by 568 days.

(21) Appl. No.: 18/000,429

(22) PCT Filed: Apr. 19, 2021

(86) PCT No.: PCT/US2021/027949
§ 371 (c)(1),
(2) Date: Dec. 1, 2022

(87) PCT Pub. No.: WO2021/257173
PCT Pub. Date: Dec. 23, 2021

(65) Prior Publication Data
US 2023/0286922 A1 Sep. 14, 2023

Related U.S. Application Data

(60) Provisional application No. 63/039,033, filed on Jun. 15, 2020.

(51) Int. Cl.
*C07D 233/88* (2006.01)
*A61K 31/4174* (2006.01)
*A61K 31/7048* (2006.01)
*A61P 31/04* (2006.01)

(52) U.S. Cl.
CPC ........ *C07D 233/88* (2013.01); *A61K 31/4174* (2013.01); *A61K 31/7048* (2013.01); *A61P 31/04* (2018.01)

(58) Field of Classification Search
CPC .. C07D 233/08; A61K 31/41; A61K 31/4164; A61K 31/4174
See application file for complete search history.

(56) References Cited

U.S. PATENT DOCUMENTS 11,582,970 B2 * 2/2023 Melander .................. A01P 1/00
2009/0270475 A1 10/2009 Melander et al.

FOREIGN PATENT DOCUMENTS

WO 2012135016 A2 10/2012
WO WO-2018035018 A1 * 2/2018 ......... A61K 31/4168
WO 2018169752 A1 9/2018

OTHER PUBLICATIONS

Brackett et al., "Small-Molecule Suppression of β-Lactam Resistance in Multidrug-Resistant Gram-Negative Pathogens," J Med Chem., 57(17):7450-7458, Aug. 2014.
Bunders et al., "Identification of Aryl 2-Aminoimidazoles As Biofilm Inhibitors in Gram-Negative Bacteria," Bioorg Med Chem Lett., 20(12):3797-3800, Jun. 2010.
International Search Report and Written Opinion of the ISA/US in PCT/US2021/027949, dated Sep. 9, 2021; 10pgs.
Martin et al., "Small Molecule Potentiation of Gram-Positive Selective Antibiotics against Acinetobacter baumannii," ACS Infect Dis., 5(7):1223-1230, Apr. 2019.
Minrovic et al., "A New Class of Adjuvants Enables Lower Dosing of Colistin Against Acinetobacter baumannii," ACS Infect Dis., 4(9):1368-1376, Sep. 2018.
Minrovic et al., "Second-Generation Tryptamine Derivatives Potently Sensitize Colistin Resistant Bacteria to Colistin," ACS Med Chem Lett., 10(5):828-833, Apr. 2019.
Stokes et al., "Pentamidine Sensitizes Gram-Negative Pathogens to Antibiotics and Overcomes Acquired Colistin Resistance," Nat Microbiol., 2(5):17028, Mar. 2017.

* cited by examiner

*Primary Examiner* — James D. Anderson
(74) *Attorney, Agent, or Firm* — Haukaas Fortius PLLC; Michael Haukaas

(57) ABSTRACT

We report improved adjuvant compounds that have an aryl 2-aminoimidazole structure for macrolide potentiation against a virulent strain of gram-negative bacteria, AB5075. Compounds were discovered to retain significant adjuvant activity at 10 μM, lowering the minimum inhibitory concentration (MIC) of clarithromycin (CLR) from 8-fold to 128-fold or greater. 2-Aminoimidazole compounds linked to aryl groups via either an amide or urea linker showed significantly improved activity over control compounds.

3 Claims, No Drawings

ANTIBIOTIC ADJUVANT COMPOUNDS

RELATED APPLICATIONS

This application is a National Stage filing under 35 U.S.C. § 371 of International Application No. PCT/US2021/027949 filed Apr. 19, 2021, which claims the benefit of U.S. Provisional Patent Application No. 63/039,033, filed Jun. 15, 2020, which is incorporated herein by reference.

GOVERNMENT SUPPORT

This invention was made with government support under Grant Nos. R01 GM055769 and R01 AI136904 awarded by the National Institutes of Health. The government has certain rights in the invention.

BACKGROUND OF THE INVENTION

The prevalence of infections that stem from multi-drug resistant (MDR) bacteria has significantly increased in recent years, which, in addition to a reduction in the involvement of pharmaceutical companies in antibiotic development, has severely limited currently available treatment options. Resistance toward every class of clinically prescribed antibiotics has now been observed. The Centers for Disease Control and Prevention (CDC) estimates that over 2.8 million people are infected with antibiotic-resistant bacteria each year, and approximately 35,000 deaths result from these bacterial infections. A high number of these deaths are associated with infections caused by the ESKAPE pathogens (*Enterococcus faecium, Staphylococcus aureus, Klebsiella pneumoniae, Acinetobactor baumannii, Pseudomonas aeruginosa, Enterobacter* species), where the 'ES' represents gram-positive species and the 'KAPE' pathogens represents gram-negative species. Gram-negative pathogens are of particular concern because their outer membrane (OM) is impermeable to many antibiotics, further limiting the available antibiotics for treating MDR gram-negative infections.

Despite the target being present in both gram-positive and gram-negative bacteria, macrolides are generally utilized for the treatment of gram-positive infections due to low penetration of the OM. It has been shown, however that if the OM is compromised then macrolides can become efficacious against gram-negative bacteria. For example, *A. baumannii* strains that lack lipopolysaccharide (LPS) are highly permeable and are susceptible to treatment with the macrolide antibiotic azithromycin. Compounds that are able to physically disrupt the outer membrane, such as pentamidine and polymyxin derivatives, are also able to sensitize gram-negative bacteria to macrolides.

We had reported on two small molecules that potentiate the activity of clarithromycin (CLR) against a strain of *A. baumannii* (AB5075) (*ACS Infect Dis* 2019, 5 (7), 1223). These compounds, which are referred to as antibiotic adjuvants, are relatively non-toxic to AB5075 by themselves (MICs of 100 μM); however at 30 μM, each compound reduced the minimum inhibitory concentration (MIC) of CLR by 128-fold, from 32 μg/mL to 0.25 μg/mL, while at 10 μM they reduced the CLR MIC 16-fold to 2 μg/mL. Investigations into the mechanism of action of these molecules revealed that, unlike other small molecules that compromise the outer membrane through physical disruption, these compounds antagonized colistin and altered Lipid A composition in AB5075. This suggests that alterations in LPS presentation and/or biosynthesis may underpin these adjuvants mode of action (MoA).

Accordingly, there is a need for adjuvant compounds that potentiate the activity of antibiotics and circumvent bacterial resistance mechanisms against the antibiotics.

SUMMARY

While further investigation is needed to determine the target for these molecules, we herein report a structure-activity relationship (SAR) analysis encompassing structural modifications of the reported lead compounds 1 and 2 (Scheme 1) to further optimize activity in combination with macrolide antibiotics, specifically CLR which displays the greatest enhancement in activity of the three macrolide antibiotics studied (erythromycin, azithromycin, CLR) against AB5075.

Accordingly, this disclosure provides a compound of Formula I.

(I)

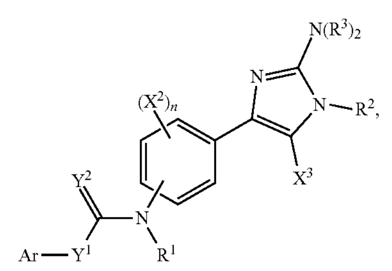

or a salt thereof; wherein

Ar is

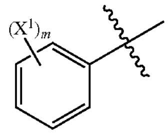

;

$R^1$ and $R^2$ are each independently H or —$(C_1\text{-}C_6)$alkyl;

each $R^3$ is independently H or —$(C_1\text{-}C_6)$alkyl;

each $X^1$ is independently halo, $CF_3$, or —$(C_1\text{-}C_6)$alkyl, wherein m is 0-5;

each $X^2$ is independently halo, $CF_3$, —$(C_1\text{-}C_6)$alkyl, or —$O(C_1\text{-}C_6)$alkyl, wherein n is 0-2;

$X^3$ is H, halo, $CF_3$, or —$(C_1\text{-}C_6)$alkyl;

$Y^1$ is absent or $NR^4$ wherein $R^4$ is H or —$(C_1\text{-}C_6)$alkyl; and $Y^2$ is O or S.

This disclosure also provides a method for treating a bacterial infection in a subject in need thereof comprising administering to the subject, concurrently or sequentially, a therapeutically effective dose of an adjuvant and a therapeutically effective dose of a macrolide antibiotic, wherein the adjuvant is the compound or composition described herein, and the bacterial infection is thereby treated.

The invention provides novel compounds of Formulas I-IV, intermediates for the synthesis of compounds of Formulas I-IV, as well as methods of preparing compounds of Formulas I-IV. The invention also provides compounds of Formulas I-IV that are useful as intermediates for the synthesis of other useful compounds. The invention provides for the use of compounds of Formulas I-IV for the manufacture of medicaments useful for the treatment of bacterial infections in a mammal, such as a human.

The invention provides for the use of the compositions described herein for use in medical therapy. The medical therapy can be treating bacterial infections. The invention also provides for the use of a composition as described herein for the manufacture of a medicament to treat a disease in a mammal, for example, a multi-drug resistant (MDR) Gram-negative or Gram-positive bacterial infection in a human. The medicament can include a pharmaceutically acceptable diluent, excipient, or carrier.

DETAILED DESCRIPTION

Approximately 1.7 million Americans develop hospital associated infections each year, resulting in more than 98,000 deaths. One of the main contributors to such infections is the gram-negative pathogen *Acinetobacter baumannii*. Recently, it was reported that aryl 2-aminoimidazole (2-AI) compounds potentiate macrolide antibiotics against a highly virulent strain of *A. baumannii*, AB5075. The two lead compounds in that report increased clarithromycin potency against AB5075 by 16-fold, lowering the minimum inhibitory concentration (MIC) from 32 to 2 μg/mL at a concentration of 10 μM. Herein, we report a structure-activity relationship study of a panel of derivatives structurally inspired by the previously reported aryl 2-AI leads. Substitutions around the core phenyl ring yielded a lead that potentiates clarithromycin by 64- and 32-fold against AB5075 at 10 and 7.5 μM, exceeding the dose response of the original lead. Additional probing of the amide linker led to the discovery of two urea containing adjuvants that suppressed clarithromycin resistance in AB5075 by 64- and 128-fold at 7.5 μM. Finally, the originally reported adjuvant was tested for its ability to suppress the evolution of resistance to clarithromycin over the course of nine consecutive days. At 30 μM, the parent compound reduced the CLR MIC from 512 to 2 μg/mL, demonstrating that the original lead was remained active against a more CLR resistant strain of AB5075.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group. The alkyl can be a monovalent hydrocarbon radical, as described and exemplified above, or it can be a divalent hydrocarbon radical (i.e., an alkylene).

An alkylene is an alkyl group having two free valences at a carbon atom or two different carbon atoms of a carbon chain. Similarly, alkenylene and alkynylene are respectively an alkene and an alkyne having two free valences at two different carbon atoms.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with a substituent described below.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms, wherein the ring skeleton comprises a 5-membered ring, a 6-membered ring, two 5-membered rings, two 6-membered rings, or a 5-membered ring fused to a 6-membered ring. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments, 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl. Substituents of the indicated groups can be those recited in a specific list of substituents described herein, or as one of skill in the art would recognize, can be one or more substituents selected from alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Suitable substituents of indicated groups can be bonded to a substituted carbon atom include F, Cl, Br, I, OR', OC(O)N(R')2, CN, CF3, OCF3, R', O, S, C(O), S(O), methylenedioxy, ethylenedioxy, N(R')2, SR', SOR', SO2R', SO2N(R')2, SO3R', C(O)R', C(O)C(O)R', C(O)CH2C(O)R', C(S)R', C(O)OR', OC(O)R', C(O)N(R')2, OC(O)N(R')2, C(S)N(R')2, (CH2)0-2NHC(O)R', N(R')N(R')C(O)R', N(R')N(R')C(O)OR', N(R')N(R')CON(R')2, N(R')SO2R', N(R')SO2N(R')2, N(R')C(O)OR', N(R')C(O)R', N(R')C(S)R', N(R')C(O)N(R')2, N(R')C(S)N(R')2, N(COR')COR', N(OR')R', C(=NH)N(R')2, C(O)N(OR')R', or C(=NOR')R' wherein R' can be hydrogen or a carbon-based moiety (e.g., (C1-C6)alkyl), and wherein the carbon-based moiety can itself be further substituted. When a substituent is monovalent, such as, for example, F or Cl, it is bonded to the atom it is substituting by a single bond. When a substituent is divalent, such as O, it is bonded to the atom it is substituting by a double bond; for example, a carbon atom substituted with O forms a carbonyl group, C=O.

The term "$IC_{50}$" is generally defined as the concentration required to kill 50% of the cells in 24 hours.

Embodiments of the Invention

This disclosure provides a compound of Formula I:

(I)

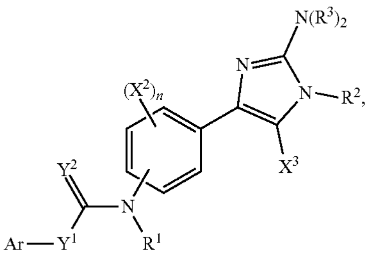

or a salt thereof; wherein

Ar is

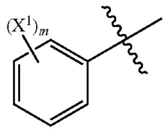

;

$R^1$ and $R^2$ are each independently H or $-(C_1-C_6)$alkyl;

each $R^3$ is independently H or $-(C_1-C_6)$alkyl;

each $X^1$ is independently halo, $CF_3$, or $-(C_1-C_6)$alkyl, wherein m is 0-5;

each $X^2$ is independently halo, $CF_3$, $-(C_1-C_6)$alkyl, or $-O(C_1-C_6)$alkyl, wherein n is 0-2;

$X^3$ is H, halo, $CF_3$, or $-(C_1-C_6)$alkyl;

$Y^1$ is absent or $NR^4$ wherein $R^4$ is H or $-(C_1-C_6)$alkyl; and $Y^2$ is O or S.

In some embodiments, $R^1$, $R^2$, and each $R^3$ is H. In some embodiments, $Y^1$ is absent. In some embodiments, $Y^1$ is $NR^4$ and $R^4$ is H. In some embodiments, $Y^2$ is O. In some embodiments, $X^1$ is in the ortho, meta, or para position when m is 1. In some other embodiments, when m is 2-4, each $X^1$ is in a combination of the ortho, ortho prime, meta, meta prime, or para positions. In some embodiments, $X^2$ is in the ortho, meta, or para position, relative to the imidazolyl moiety, when n is 1. In some other embodiments, when n is 2, each $X^2$ is in a combination of the ortho, ortho prime, meta, meta prime, or para positions, relative to the imidazolyl moiety.

In some embodiments, $X^3$ is H. In some embodiments, $X^3$ is F. In some embodiments, m is 2 or 3. In some embodiments, n is 1 or 2. In some embodiments, the amido moiety is ortho, meta, or para relative to the imidazolyl moiety. In some embodiments, each $X^1$ is independently chloro, bromo, or $CF_3$, and m is 2 or 3. In some embodiments, each $X^2$ is fluoro, and n is 0, 1, or 2.

In some embodiments, the compound is represented by Formula II:

(II)

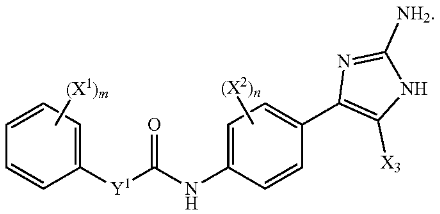

In some embodiments, the compound is represented by Formula III:

(III)

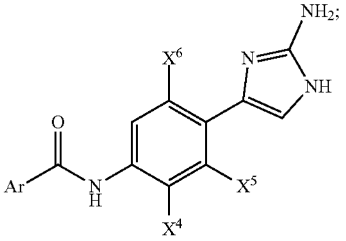

wherein $X^4$, $X^5$ and $X^6$ are each independently H, F, $CH_3$, or $OCH_3$.

In some embodiments, the compound is any one of compounds 4a-4y:

wherein $X^4$, $X^5$ and $X^6$ are H; and Ar is:

4a

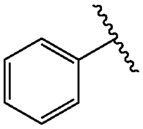

4b

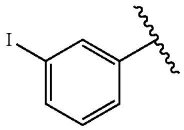

4c

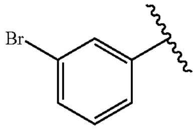

4d

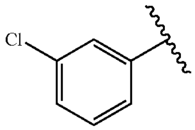

-continued

4e

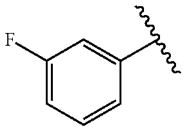

4f

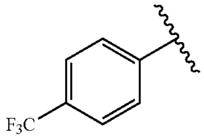

4g

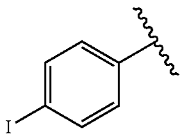

4h

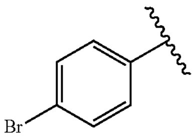

4i

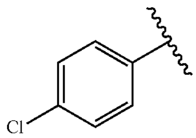

4j

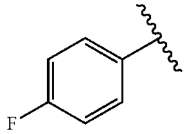

4k

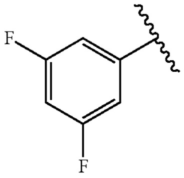

4l

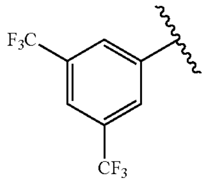

4m

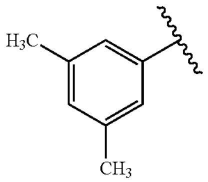

-continued

4n

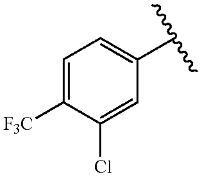

4o

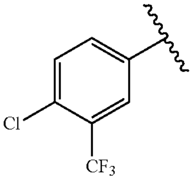

4p

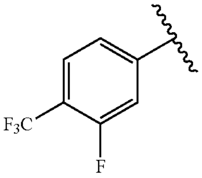

4q

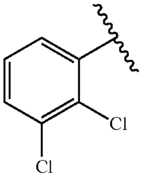

4r

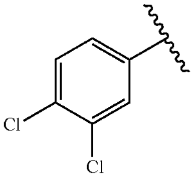

4s

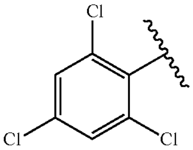

4t

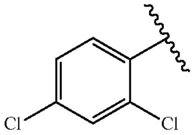

4u

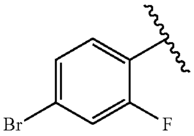

4v

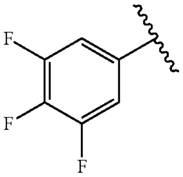

-continued

4w

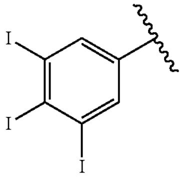

4x

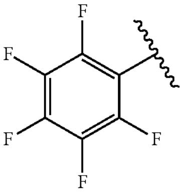

or

4y

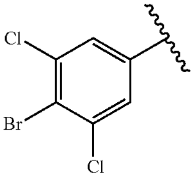

.

In some embodiments, the compound is any one of compounds 6a, 6b, 10a-10e, and 13:

wherein Ar is

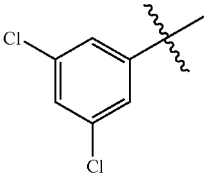

;

and $X^4$ is $OCH_3$, and $X^5$ and $X^6$ are H (6a);

$X^4$ and $X^6$ are H, and $X^5$ is $CH_3$ (6b);

$X^4$ is $CH_3$, and $X^5$ and $X^6$ are H (10a);

$X^4$ is Cl, and $X^5$ and $X^6$ are H (10b);

$X^4$ is F, and $X^5$ and $X^6$ are H (10c);

$X^4$ and $X^6$ are H, and $X^5$ is F (10d);

$X^4$ and $X^6$ are H, and $X^5$ is Cl (10e); or $X^4$ is H, and $X^5$ and $X^6$ are F (13).

In some embodiments, the compound is any one of compounds 15a, 15b, 17a, and 17b:

wherein $X^4$ and $X^6$ are H, and $X^5$ is F; and Ar is:

(15a)

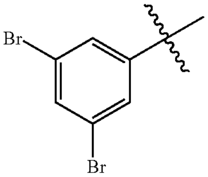

;

-continued
(15b)
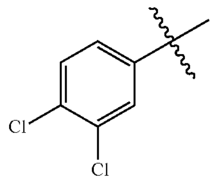
;
(17a)
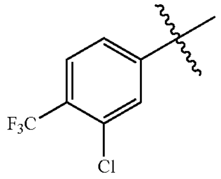
; or
(17b)
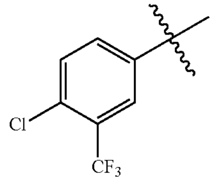
.
In some embodiments, the compound is represented by Formula IV:
(IV)
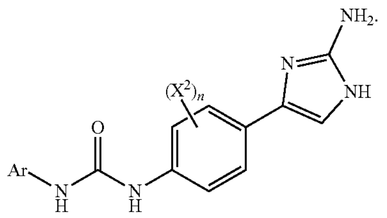
In some embodiments, the compound is any one of compounds 20a-20c:
wherein n is 0; and Ar is:
(20a)
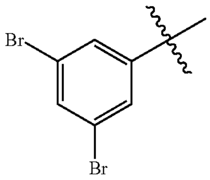
;
(20b)
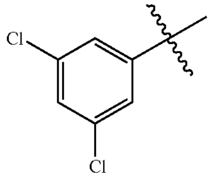
; or
-continued
(20c)
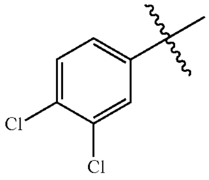
.
In some embodiments, the compound is:
4y
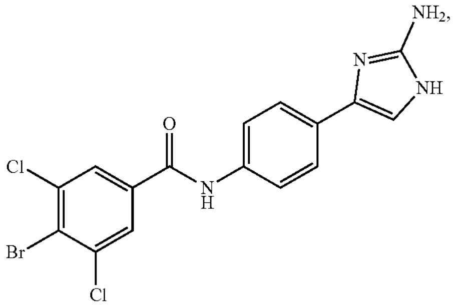
10d
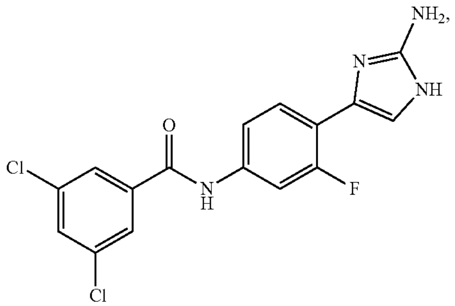
15b
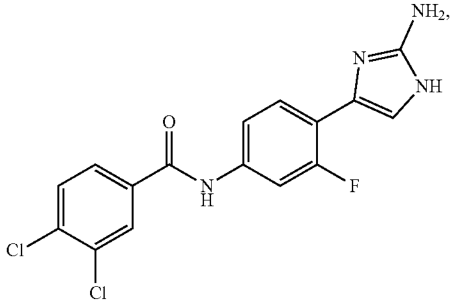
18
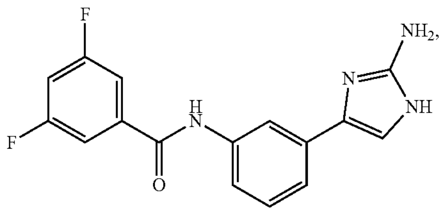

-continued

19

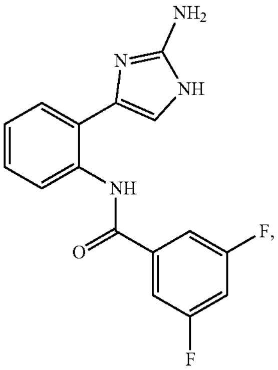

or

20a

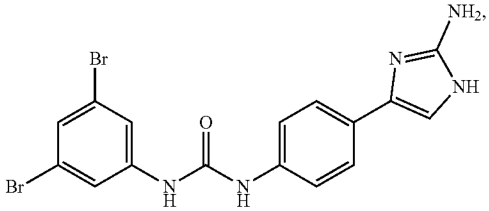

Also, this disclosure provides a composition comprising a compound disclosed herein and a pharmaceutically acceptable buffer, carrier, diluent, or excipient. In some embodiments, the composition further comprises an antibiotic.

Additionally, this disclosure provides a method for treating a bacterial infection in a subject in need thereof comprising administering to the subject, concurrently or sequentially, a therapeutically effective dose of an adjuvant and a therapeutically effective dose of a macrolide antibiotic, wherein the adjuvant is a compound or composition disclosed herein, and the bacterial infection is thereby treated.

In some embodiments, the adjuvant is:

4y

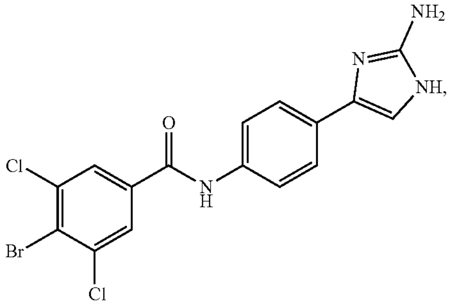

10d

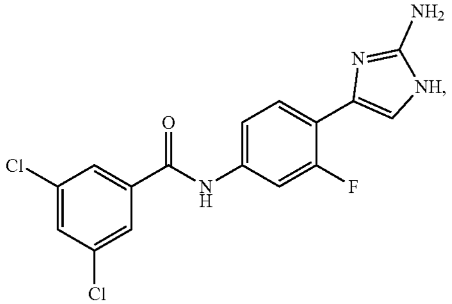

-continued

15b

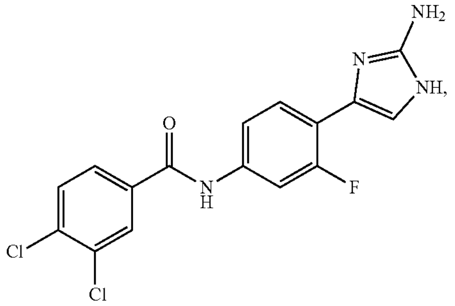

or

20a

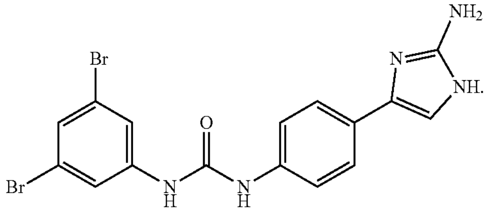

In various embodiments, the adjuvant is:

1

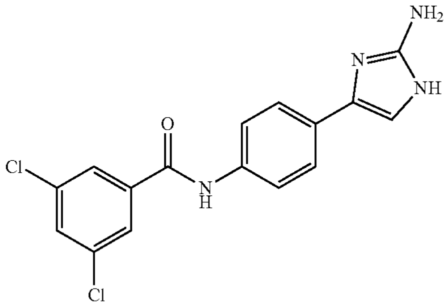

2

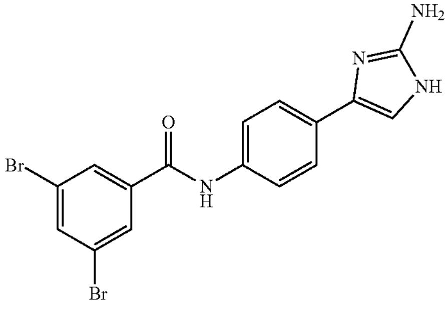

4h

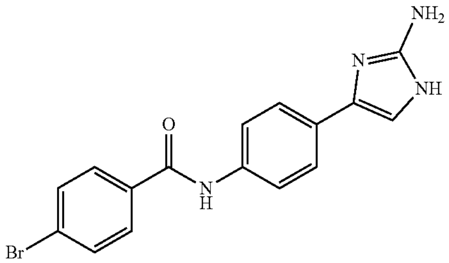

-continued

4j

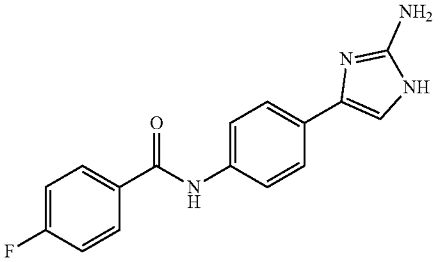

4p

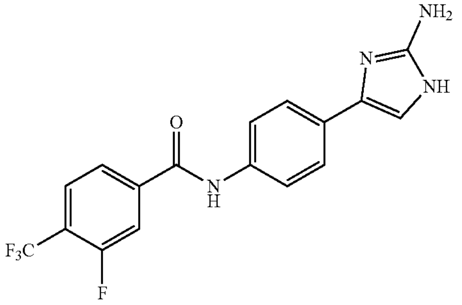

4q

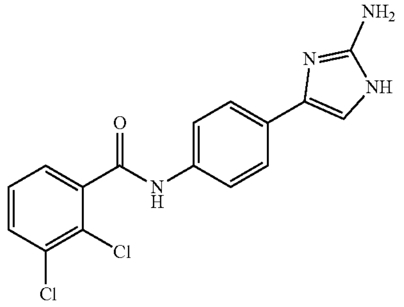

or

4f

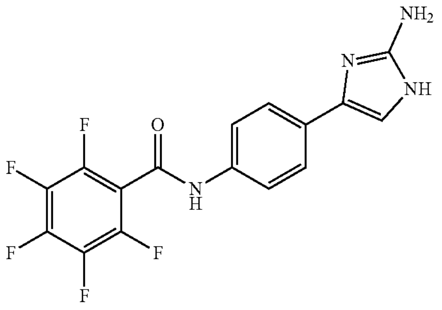

In some embodiments, the macrolide antibiotic is clarithromycin. In some embodiments, the bacterial infection is a Gram-negative bacterial infection. In some embodiments, the bacterial infection is *Acinetobactor baumannii*. In some embodiments, the subject has a systemic concentration of the adjuvant of about 0.1 micromolar to about 200 micromolar, after the administration of the adjuvant. In some embodiments, the subject has a systemic concentration of the macrolide antibiotic of about 0.1 microgram/milliliter to about 100 microgram/milliliter, after the administration of the macrolide antibiotic.

Results and Discussion

To perform analog synthesis, we divided the lead molecules into three regions: region 1, the aryl tail, region 2, the phenyl core, and region 3, the amide linker (Scheme 1).

First, we elected to modify the aryl tail of compound 1 in an attempt to delineate the importance of electron-withdrawing and/or inductive effects. Next, we introduced various functional groups on the phenyl core while maintaining the 3.5-dichloro substituent in the aryl tail. After identifying structural components in each region that augmented activity, we combined the most effective phenyl core modification with aryl tails that had shown augmented activity with CLR. Finally, a brief SAR was performed modifying the original amide linker.

Scheme 1. Initial lead aryl 2-aminoimidazole adjuvants 1 and 2.

1

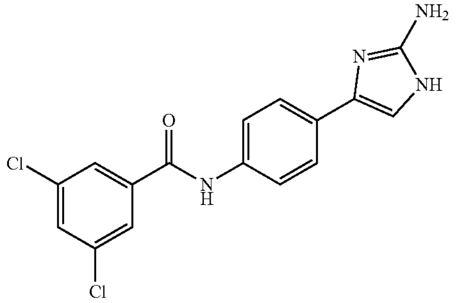

2

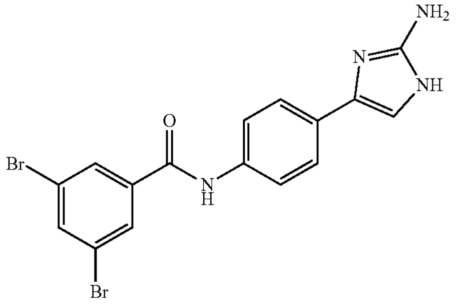

We initiated our study by screening additional analogs of 1 and 2 for CLR potentiation against AB5075 (Scheme 1). Seventeen of the 25 aryl 2-AI analogs had been previously synthesized and screened for potentiation of β-lactam antibiotics against gram-negative bacteria (*J Med Chem* 2014, 57 (17), 7450). The other analogs were accessed through intermediate 3 by acylation with the appropriate acid chloride, TFA-mediated removal of the Boc-groups, and finally counter ion exchange. Once the pilot library was completed, each compound was first analyzed individually for stand-alone toxicity against AB5075 by determining the MIC (Table 1A). Of the 25 analogs, one registered an MIC of 25 μM (4n), two returned an MIC of 50 μM (4l, 4p), four displayed an MIC of 100 μM (4o, 4r, 4s, and 4v), while the MIC of the rest of the analogs were ≥200 μM. To test for potentiation, the MIC of CLR against AB5075 was determined in the absence or presence of each compound dosed at 30% their MIC or 30 μM, whichever was lower (Table 1A). Each analog was compared to the activity of compounds 1 and 2 at 30 μM.

Scheme 2. Aryl tail modifications of previously reported adjuvants 1 and 2.

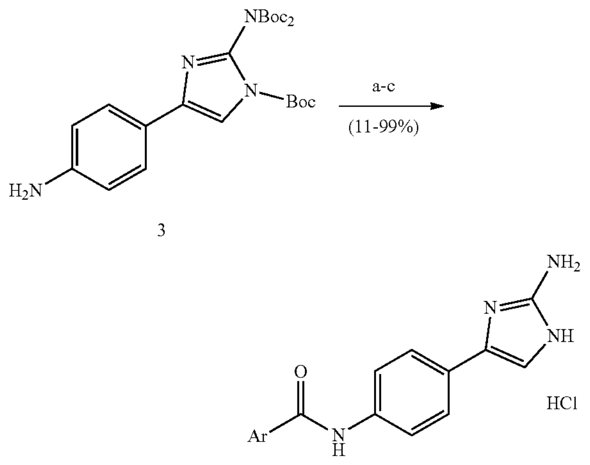

3

4a-y

Reagents and conditions: a) ArCOCl, $K_3PO_4$, THF, 25° C., 16 h; b) TFA, DCM, 25° C., 3 h; c) 6M HCl, MeOH, 25° C., 5 min.

Ar =

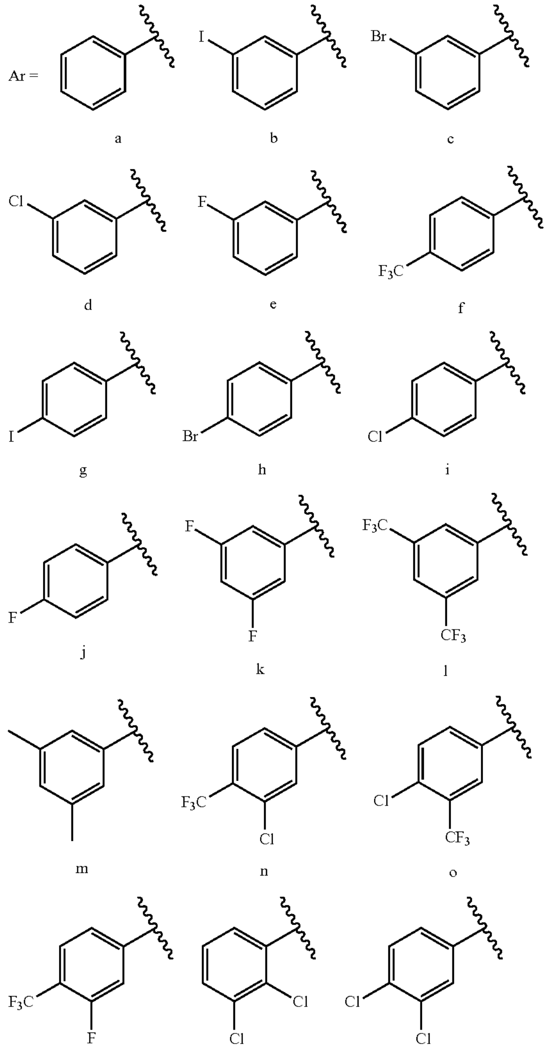

a b c d e f g h i j k l m n o p q r

-continued

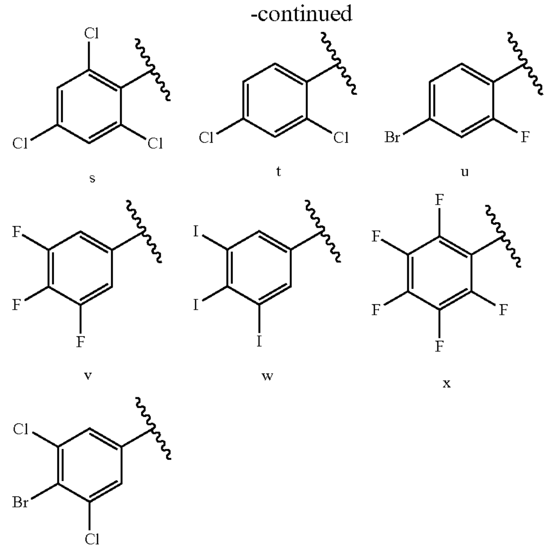

s t u v w x y

First, we noted that removal of the halides (4a) abolished activity (Scheme 2, Table 1A). We also observed that di-substitution patterns on the aryl tail were typically more active and achieved greater CLR potentiation when compared to mono-substituted compounds. The only mono-substituted compounds that displayed CLR potentiation at 30 μM were mono-chlorinated compounds (4d, 4i) and one mono-brominated compound (4h).

TABLE 1A

CLR potentiation against AB5075 for compounds with varying aryl tails.

| Compound | MIC (μM) | Concentration Tested (μM) | CLR MIC (μg/mL) |
|---|---|---|---|
| — | — | — | 32 |
| 4a | >200 | 30 | 16 |
| 4b | >200 | 30 | 32 |
| 4c | >200 | 30 | 32 |
| 4d | 200 | 30 | 1 |
| 4e | >200 | 30 | 16 |
| 4f | >200 | 30 | 32 |
| 4g | >200 | 30 | 16 |
| 4h | >200 | 30 | 4 |
| 4i | >200 | 30 | 1 |
| 4j | >200 | 30 | 8 |
| 4k | >200 | 30 | 4 |
| 4l | 50 | 15 | 8 |
| 4m | >200 | 30 | 2 |
| 4n | 25 | 7.5 | 2 |
| 4o | 100 | 15 | 0.5 |
| 4p | 50 | 15 | 0.5 |
| 4q | >200 | 30 | 8 |
| 4r | 100 | 30 | 0.5 |
| 4s | 100 | 30 | 0.5 |
| 4t | >200 | 30 | 4 |
| 4u | >200 | 30 | 2 |
| 4v | 100 | 30 | 1 |
| 4w | >200 | 30 | 32 |
| 4x | >200 | 30 | 4 |
| 4y | 200 | 30 | 0.25 |
| — | — | — | — |

Compounds 4k-m, which incorporated a 3,5-disubstiution pattern, allowed a comparison of the effects of replacing Cl/Br with F, Cl/Br with $CF_3$, and Cl for $CH_3$ (steric isostere). Compound 4k only exhibited an eight-fold reduction in the MIC of CLR at 30 μM, while compounds 4l and 4m, also exhibited relatively modest activity, returning CLR MICs of 8 and 2 μg/mL respectively at 15 μM and 30 μM.

Since chlorination appeared to be a promising halogenation choice for adjuvant activity, the positioning of the dichloro substitution pattern was evaluated next. Dichlorination at the 2,3-positions, seen in compound 4q, resulted in only four-fold potentiation of CLR at 30 μM, while compound 4r in which the chloro substituents were moved to the 3,4-position displayed a 64-fold reduction in the MIC of CLR at 30 μM. Compound 4t, which placed the chloro residues at the 2,4-position, exhibited only an eight-fold reduction in the MIC of CLR at 30 μM. Analysis of structure-function of tri- and multi-halogenated patterns on the aryl tail showed that 4r, 4s, and 4y displayed comparative CLR potentiation to the original adjuvants 1 and 2 when dosed at 30 μM.

Next, a dose response study was conducted with nine of the most active compounds (4d, 4i, 411, 4o, 4p, 4r, 4s, 4u, 4v, and 4y) to determine CLR potentiation as a function of compound concentration (Table 11B). At 10 μM, 4o, 4p, and 4r showed comparable activity to the original leads 1 and 2, returning CLR MICs of 2, 1, and 4 μg/mL respectively. Compound 4y, however, was significantly more active maintaining a CLR MIC of 0.25 μg/mL (128-fold reduction) at 10 μM.

TABLE 1B

Dose-response of active aryl tails for CLR potentiation against AB5075.

| Compound | Concentration Tested (μM) | CLR MIC (μg/mL) | Compound | Concentration Tested (μM) | CLR MIC (μg/mL) |
|---|---|---|---|---|---|
| — | — | 32 | — | — | 32 |
| 4d | 20 | 4 | 4r | 20 | 0.5 |
| | 10 | 16 | | 10 | 4 |
| | | | | 7.5 | 8 |
| 4i | 20 | 4 | 4s | 25 | 8 |
| | 10 | 16 | | 20 | 16 |
| | | | | 10 | 32 |
| 4n | 5 | 16 | 4u | 20 | 16 |
| | | | | 10 | 32 |
| 4o | 10 | 2 | 4v | 20 | 8 |
| | 7.5 | 8 | | 10 | 32 |
| 4p | 10 | 1 | 4y | 20 | 0.25 |
| | 7.5 | 4 | | 10 | 0.25 |
| | 5 | 16 | | 7.5 | 8 |

To probe the SAR of region 2, the original 3,5-dichloro aryl tail was held constant while various functional groups were introduced on the phenyl core. The synthetic approach to these analogs is outlined in Scheme 3. Anilines 7a-e were alloc-protected using allyl chloroformate in a biphasic solvent system under basic conditions at 0° C. to afford compounds 8a-e. Compounds 8a-e and 5a-b were then converted into their corresponding acid chlorides using oxalyl chloride and a catalytic amount of DMF at 0° C. Each acid chloride was reacted with diazomethane at 0° C. for two hours followed by addition of hydrobromic acid to generate the corresponding α-bromo-ketone. The α-bromo-ketones were then cyclized with Boc-guanidine to deliver the corresponding mono-Boc-protected 2-AI compounds 9a-e. The alloc protecting groups of 9a-e were then removed by treatment with tetrakis(triphenylphospine)palladium(0) and sodium borohydride. Each aniline was then immediately acylated using commercially available 3,5-dichlorobenzyl chloride under basic conditions, that, following Boc-deprotections using trifluoroacetic acid and subsequent conversion to the hydrochloric acid salt, afforded compounds 10a-e. Intermediates that contained a nitro group as the latent aniline were reduced using palladium on carbon and hydrogen gas. Acylation, Boc-deprotection and ion exchange as above yielded compounds 6a-b.

Scheme 3. Phenyl core modification of compounds 1 and 2.

A

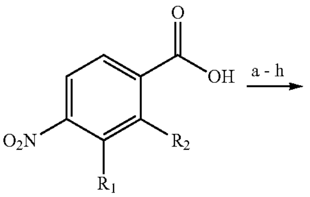

5a, R1= OCH3 R2= H
5b, R1= H R2= CH3

-continued

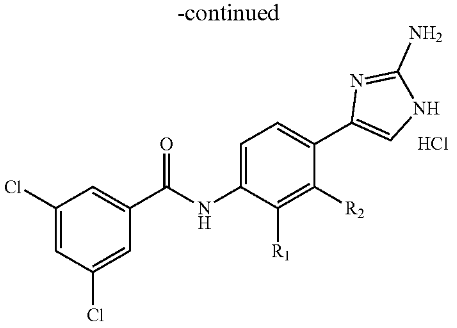

6a, R1= OCH3 R2= H, 95%
6b, R1= H R2= CH3, 93%

-continued

B

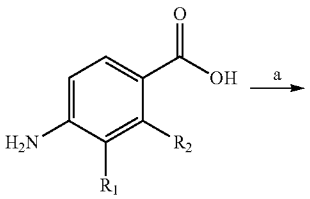

7a, R1= CH3 R2= H
7b, R1= Cl R2= H
7c, R1= F R2= H
7d, R1= H R2= F
7e, R1= H R2= Cl

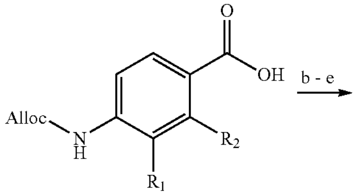

8a - 8e
(83-92%)

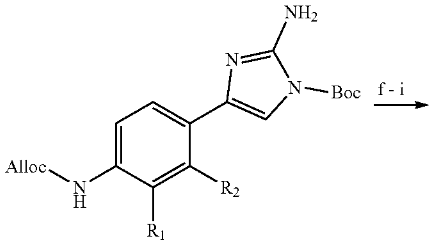

9a - 9e
(27-54%)

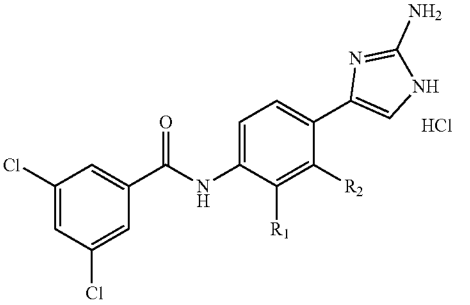

10a - 10e
(89-98%)

C

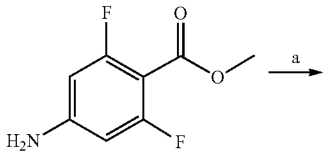

11

-continued

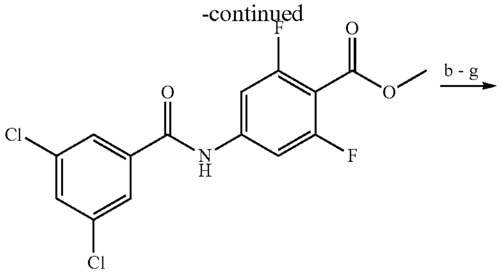

12 (not isolated)

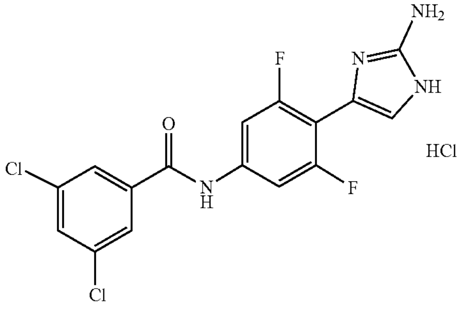

13 (92%)

Reagents and conditions for 3A: a) $(COCl)_2$, $DMF_{cat}$, DCM, 0° C., 2 h; b) $CH_2N_2$, $Et_2O$, DCM, 0° C., 1.5 h; c) HBr, 0° C., 30 min; d)Boc-guanidine, THF, 56° C., 3 h; e) $H_2$, 10% Pd/C, MeOH, 25° C., 16 h; f) 3,5-dichlorobenzoyl chloride, $K_3PO_4$, THF, 0° C., 16 h; g) TFA, DCM, 25° C., 3 h; h) 6M HCl, MeOH, 25° C., 5 min. Reagents and conditions for 3B: a) allyl chloroformate, $NaHCO_3$, DIPEA, 1,4-dioxane/$H_2O$, 0° C., 16 h; b) (COCl)2, $DMF_{cat}$, DCM, 0° C., 2 h; c) $CH_2N_2$, $Et_2O$, DCM, 0° C., 1.5 h; d) HBr, 0° C., 30 min; e) Boc-guanidine, THF, 56° C., 3 h; f) $Pd(PPh_3)_4$, $NaBH_4$, EtOH, 25° C., 4 h; g) 3,5-dichlorobenzoyl chloride, $K_3PO_4$, THF, 0° C, 16 h; h) TFA, DCM, 25° C., 3 h; i) 6M HCl, MeOH. 25° C., 5 min. Difluoro modification on phenyl core of lead adjuvant l0d. Reagents and conditions for 3C: a) 3,5-dichlorobenzoyl chloride, $K_3PO_4$, THF, 0° C., 16 h; b) 5M NaOH, MeOH/$H_2O$, 25° C., 3 h; c) $(COCl)_2$ $DMF_{cat}$, DCM, 0° C., 2 h; d) $CH_2N_2$, $Et_2O$, DCM, 0° C., 1.5 h; e) HBr, 0° C., 30 min; f) Boc-guanidine, THF, 56° C., 3 h; g) TFA, DCM, 25° C., 3 h, then 6 M HCl, MeOH, 25° C., 5 min.

As detailed above, all compounds were first screened against AB5075 alone to determine their MICs followed by an initial screen of each compound at ≤30% their MIC in combination with CLR (Table 2). Except for 6a, which returned a standalone MIC of 100 μM, all derivatives were essentially non-toxic showing MIC values >200 μM. When the carbon ortho to the amide linker ($R_1$, Scheme 3) contained either a methyl or methoxy substituent, similar levels of CLR potentiation was noted in comparison to compounds 1 and 2. Both methyl and methoxy compounds, 10a and 6a, displayed a 64-fold reduction in CLR MIC at 30 μM compared to parent 128-fold activity at 30 μM. When either Cl or F is placed at this position, activity decreased significantly, with only a two- and four-fold reduction in CLR MIC observed for compounds 10b and 10c respectively at 30 μM. We noted a substantially different trend when substituents were placed meta to the amide linker ($R_2$, Scheme 3). Derivatives containing a chloro (10e), fluoro (10d), or methyl (6b) potentiated CLR activity by a similar degree to compound 1, lowering the MIC of CLR by 64-fold, from 32 to 0.5 μg/mL, when dosed at 30 μM.

The five analogs (6a, 6b, 10a, 10d, and 10e) showing comparable activity to 1 were then subjected to a dose response study (Table 2). Compounds 6a, 6b, 10a, and 10e were not as active as 1 at 10 μM, effecting an MIC reduction of two-, four-, two-, and four-fold respectively. The fluoro analog 10d, however, surpassed the activity of 1 and displayed a 64-fold reduction of the CLR MIC at 10 μM.

TABLE 2

CLR potentiation data against AB5075 using phenyl core derivatives 6a-b and 10a-e.

| Compound | $R_1$ | $R_2$ | Compound MIC (µM) | Concentration Tested (µM) | CLR MIC (µg/mL) | Fold Reduction |
|---|---|---|---|---|---|---|
| — | — | — | — | — | 32 | — |
| 6a | $OCH_3$ | H | 100 | 30 | 0.5 | 64 |
| | | | | 20 | 4 | 8 |
| | | | | 10 | 16 | 2 |
| 6b | H | $CH_3$ | >200 | 30 | 0.5 | 64 |
| | | | | 20 | 0.5 | 64 |
| | | | | 10 | 8 | 4 |
| 10a | $CH_3$ | H | >200 | 30 | 0.5 | 64 |
| | | | | 20 | 1 | 32 |
| | | | | 10 | 16 | 2 |
| 10b | Cl | H | >200 | 30 | 16 | 2 |
| 10c | F | H | >200 | 30 | 8 | 4 |
| 10d | H | F | >200 | 30 | 0.25 | 128 |
| | | | | 20 | 0.25 | 128 |
| | | | | 10 | 0.5 | 64 |
| | | | | 7.5 | 4 | 8 |
| | | | | 5 | 8 | 4 |
| 10e | H | Cl | >200 | 30 | 0.5 | 64 |
| | | | | 20 | 0.5 | 64 |
| | | | | 10 | 8 | 4 |

Given the activity of the mono-fluoro compound (10d), the difluoro analogue 13, was synthesized to probe if either symmetry or additional electronic effects would further modulate activity (Scheme 3C). Interestingly, compound 13 was essentially inactive at 10 µM, displaying only a two-fold reduction in the MIC of CLR. At 20 and 30 µM, compound 13 lowered the MIC of CLR to 8 and 4 µg/mL, respectively.

As the mono-fluoro analog 10d was significantly less toxic to AB5075 in comparison to 1 and 2, we probed whether this type of modification could attenuate the stand-alone toxicity of some of the initial tail derivatives we studied. To explore this, we chose some of the aryl tails that exhibited the ability to potentiate CLR yet were also more toxic, registering standalone MIC values (i.e. no antibiotic added) of <100 µM. We postulated that the addition of a fluoro substituent would reduce the overall toxicity of these adjuvants while either retaining or improving activity with CLR against ABS5075.

Scheme 4. Evaluation of active tails in combination with fluorinated phenyl core.

A

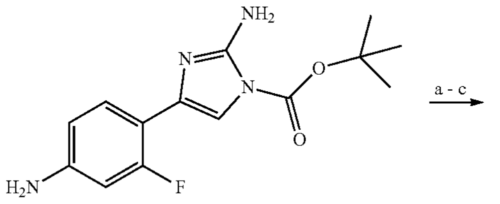

14

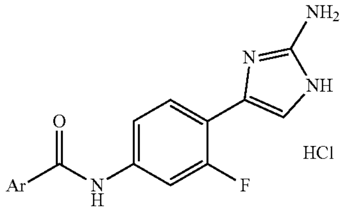

15a-b

-continued

B

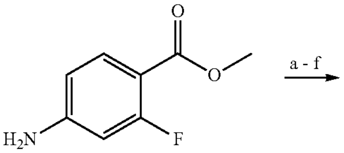

16

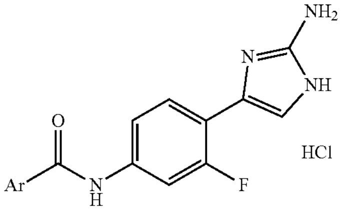

17a-b

Reagents and conditions: Scheme 4A protocol: a) ArCOCl, $K_3PO_4$, THF, 25° C., 16 h; b) TFA, DCM, 25° C., 3 h; c) 6M HCl, MeOH, 25° C., 5 min. Scheme 4B protocol: a) ArCOCl, $K_3PO_4$, THF, 25° C., 16 h; b) 5M NaOH, MeOH/$H_2O$, 25° C., 3 h; c) $(COCl)_2$, $DMF_{cat}$, DCM, 0° C., 2 h; d) $CH_2N_2$, $Et_2O$, DCM, 0° C., 1.5 h; d) HBr, 0° C., 30 min; e) Boc-guanidine, THF, 56° C., 3 h; f) TFA, DCM, 25° C., 3 h, then 6M HCl, MeOH, 25° C., 5 min.

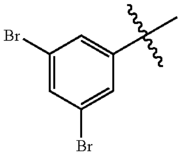

15a, 83%

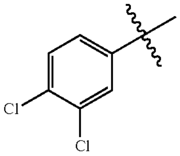

15b, 96%

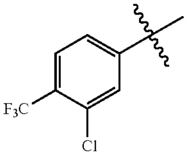

17a, 90%

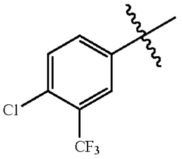

17b, 35%

The aryl tail from compound 2 in Scheme 1 was chosen first for further analog synthesis and was accessed by coupling 3,5-dibromobenzoyl chloride to mono-Boc-protected 2-AI aniline 14. After TFA-mediated Boc-deprotection followed by counter ion exchange, the fluorinated analog of 2 (15a) was screened for standalone toxicity and CLR potentiation (Scheme 4). Fluorination did indeed attenuate toxicity as 15a returned an MIC of >200 μM (compound 2 has a standalone MIC of 100 μM); however, it also compromised adjuvant activity. At 30 μM, compound 15a only reduced the CLR MIC 16-fold against AB5075 (Table 3), while compound 2 effected a 128-fold reduction at the same concentration.

The 3,4-dichlorobenzoyl tail 15b showed both a reduction in the standalone toxicity and improvement in CLR potentiation over the original motif 4r. Compound 15b afforded a standalone MIC of >200 μM (vs. 100 μM for 4r) and delivered a 32-fold reduction in CLR at a concentration of 7.5 μM, exceeding the activity of the parent compound 4r and as well as 10d. When the activity of 17a and 17b were directly compared to their non-fluorinated variants 4n and 4o, we noted that standalone toxicity was essentially unchanged (two-fold changes are not considered to be significant in a standard MIC assay). The ability of 17a to potentiate CLR activity at 7.5 μM was severely compromised in comparison to compound 4n, showing an insignificant two-fold reduction in the MIC of CLR compared to a 16-fold reduction at 7.5 μM for 4n. The adjuvant activity of compound 17b was identical to compound 4o (Table 1A, 1B, and 3).

TABLE 3

CLR potentiation data for compounds 15a-b, 17a-b, and 20a-c against AB5075.

| Compound | Compound MIC (μM) | Concentration Tested (μM) | CLR MIC (μg/mL) | Fold Reduction |
|---|---|---|---|---|
| — | — | — | 32 | — |
| 15a | >200 | 30 | 2 | 16 |
| | | 20 | 8 | 4 |
| | | 10 | 16 | 2 |
| 15b | >200 | 30 | 0.5 | 64 |
| | | 20 | 0.5 | 64 |
| | | 10 | 0.5 | 64 |
| | | 7.5 | 1 | 32 |
| | | 5 | 8 | 4 |
| 17a | 50 | 15 | 0.25 | 128 |
| | | 10 | 8 | 4 |
| | | 7.5 | 16 | 2 |
| 17b | 50 | 15 | 0.25 | 128 |
| | | 10 | 2 | 16 |
| | | 7.5 | 8 | 4 |
| 20a | 50 | 15 | 0.125 | 256 |
| | | 7.5 | 0.25 | 128 |
| | | 5 | 4 | 8 |
| 20b | 25 | 7.5 | 0.5 | 64 |
| | | 5 | 8 | 4 |
| 20c | 100 | 30 | ≤0.0625 | ≥512 |
| | | 20 | ≤0.0625 | ≥512 |
| | | 10 | 0.25 | 128 |
| | | 7.5 | 2 | 16 |
| | | 5 | 8 | 4 |

We had described related aryl 2-AI analogs that inhibit *E. coli* biofilm formation (*Bioorg Med Chem Lett* 2010, 20 (12), 3797). Within that report, compound 4k was determined to be the lead biofilm inhibitor, indicating that biofilm inhibition activity was greater when the amide linker of the 3,5-difluoro aryl tail was para in relation to the 2-AI head group opposed to meta (18) or ortho (19) (Scheme 5). We screened these same compounds for CLR potentiation against AB5075 and observed a similar trend, with the para amide linker 4k (highest adjuvant activity) >meta amide linker 18>ortho amide linker 19 (lowest adjuvant activity), when dosed at 30 μM (Scheme 5). Based on this we maintained the para position and explored diversifying the linker itself instead. We focused on incorporating a urea due to past reports showing that urea linkers are active in the context of antibiotic potentiation against gram-negative species, including *A. baumannii.*

Scheme 5. Previously reported 3,5-difluoro aryl 2-AI analogs with varying amide linker connectivity to the phenyl core.

4k

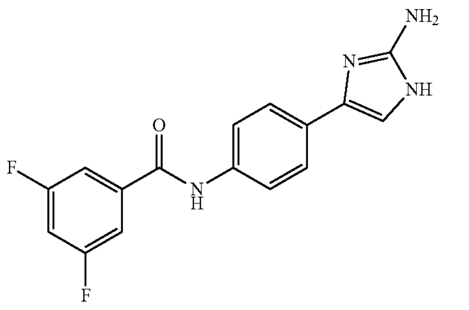

Compound MIC = >200 μM
CLR MIC + 30 μM = 4 μg/mL

18

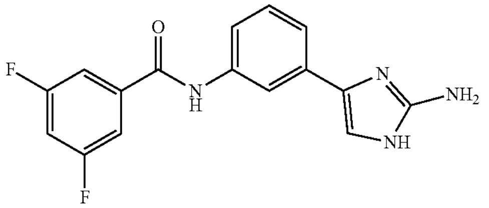

Compound MIC = >200 μM
CLR MIC + 30 μM = 16 μg/mL

19

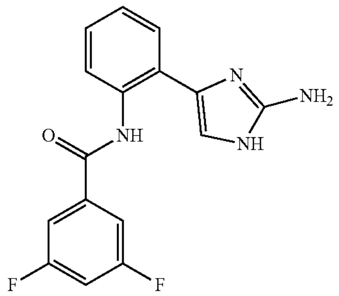

Compound MIC = >200 μM
CLR MIC + 30 μM = 32 μg/mL

Three of the most active aryl tails from the initial screenings, the aryl tails seen in compounds 1, 2, and 4r, were utilized for the synthesis of para urea derivatives (Scheme 6). Compounds 20a-c were synthesized by converting the 2-AI aniline intermediate 3 into its corresponding isocyanate using sodium carbonate and triphosgene in a biphasic solvent system at room temperature. Each isocyanate was then reacted with the appropriate halogenated aniline derivative to deliver the tri-Boc protected 2-AI intermediates. Finally, each urea derivative was exposed to trifluoroacetic acid to remove the Boc protecting groups and converted to the hydrochloric acid salt for biological testing (Scheme 6).

Scheme 6. Linker modification of active CLR adjuvants 1, 2, and 4r.

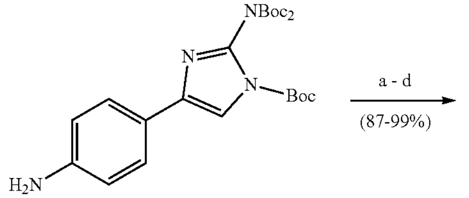

3

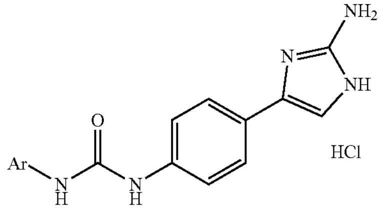

20a-c

Reagents and conditions: a) $Na_2CO_3$, $H_2O$, DCM, then triphosgene, 25° C., 2 h; b) $ArNH_2$, DCM, 25° C., 1 h; c) TFA, DCM, 25° C., 3 h; d) 6M HCl, MeOH, 25° C., 5 min.

Ar =

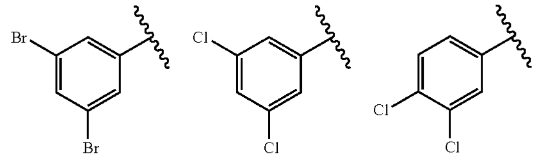

a b c

Modification of the amide linker to a urea led to an increase in adjuvant activity, yet at the cost of increasing their standalone toxicity toward AB5075 (Table 3). All three urea analogs 20a-c potentiate CLR≥16-fold at concentrations as low as 7.5 μM, with 20a showing the greatest CLR potentiation of 128-fold and becoming our lead urea derivative (Table 3). However, compounds 20a and 20b displayed higher toxicity, returning MIC values of 50 and 25 μM, respectively. The least toxic urea was compound 20c, which displayed a standalone MIC of 100 μM. Compound 20c had superior adjuvant activity at 30 μM of all of the screened compounds, including the amide linkers, lowering the MIC of CLR to ≤0.0625 μg/mL (≥512-fold, lowest concentration tested). Interestingly, when compound 20c was dosed at 7.5 μM, its adjuvant activity was comparable to the most active amide linker 15b activity, lowering the MIC of CLR by 16-fold from 32 to 2 μg/mL (Table 3).

TABLE 4

Minimum inhibitory concentration data against AB isolates.

| *A. baumannii* strain | Compound 15b (μM) | Compound 20a (μM) | CLR MIC (μg/mL) |
|---|---|---|---|
| 3560 | 50 | 25 | 32 |
| 3785 | 200 | 50 | 64 |
| 3806 | 200 | 25 | 16 |
| 3927 | >200 | 100 | 32 |
| 4025 | 100 | 100 | 64 |
| 4026 | 100 | 50 | 64 |
| 4027 | 200 | 50 | 64 |
| 4052 | >200 | 50 | 32 |
| 4269 | >200 | 50 | 32 |
| 4448 | >200 | 100 | 32 |
| 4456 | 50 | 25 | 32 |
| 4490 | >200 | 100 | 32 |
| 4498 | 100 | 50 | 64 |

TABLE 4-continued

Minimum inhibitory concentration data against AB isolates.

| *A. baumannii* strain | Compound 15b (μM) | Compound 20a (μM) | CLR MIC (μg/mL) |
|---|---|---|---|
| 4795 | 100 | 25 | 32 |
| 4857 | 50 | 50 | 64 |
| 4878 | 200 | 50 | 32 |
| 4957 | >200 | 50 | 32 |
| 4991 | >200 | 50 | 32 |
| 5001 | >200 | 50 | 32 |
| 5197 | >200 | 25 | 64 |
| 5256 | >200 | 25 | 32 |
| 5711 | >200 | 25 | 64 |
| 8967 | >200 | 100 | 16 |

In our initial report describing the macrolide potentiation activity of adjuvants 1 and 2, we examined their activity against a panel of *A. baumannii* isolates that encompasses all major and most minor clinically relevant clades. Both adjuvants suppressed macrolide resistance in 23 different AB strains at 30 μM, lowering CLR MIC values to ≤0.125 to 1 μg/mL. Since the amide linker compound 15b and the urea analog 20a displayed greater CLR potentiation than compounds 1 and 2 in A1B5075, we chose to screen the same 23 isolates at lower concentrations with compounds 15b and 20a (Table 5). To begin, compounds 15b and 20a were screened individually to determine their standalone MIC values to ensure that toxicity is avoided during antibiotic potentiation screening (Table 4). Compound 15b returned MIC values of 50 μM in three of the AB isolates, though it was relatively non-toxic (≥100 μM) in the remaining 20 strains; therefore, compound 15b was tested at 10 μM when combined with CLR against all 23 strains. Compound 20a displayed MIC values ranging from 25 to 100 μM, thus was tested at 7.5 μM for all of the 23 AB isolates to avoid potential toxic effects. Compound 15b at 10 μM lowered the MIC of CLR in all 23 AB isolates, with reductions ranging from eight- to 32-fold (Table 5). Compound 20a at 7.5 μM exhibited even greater CLR potentiation, lowering the MIC of CLR between 16- and 128-fold in all 23 AB isolates (Table 5).

TABLE 5

Clarithromycin potentiation data against AB isolates using lead aryl 2-AI adjuvants 15b and 20a

| *A. baumannii* strain | CLR MIC (μg/mL) + 15b (10 μM) | CLR MIC (μg/mL) + 20a (7.5 μM) |
|---|---|---|
| 3560 | 2 | 1 |
| 3785 | 4 | 1 |
| 3806 | 0.5 | 0.25 |
| 3927 | 2 | 0.5 |
| 4025 | 1 | 1 |
| 4026 | 4 | 1 |
| 4027 | 1 | 1 |
| 4052 | 1 | 0.5 |
| 4269 | 2 | 2 |
| 4448 | 2 | 0.5 |
| 4456 | 2 | 1 |
| 4490 | 2 | 1 |
| 4498 | 2 | 2 |
| 4795 | 2 | 0.5 |
| 4857 | 1 | 0.5 |
| 4878 | 2 | 0.5 |
| 4957 | 4 | 0.5 |
| 4991 | 2 | 0.5 |
| 5001 | 4 | 1 |
| 5197 | 2 | 1 |
| 5256 | 1 | 0.25 |

TABLE 5-continued

Clarithromycin potentiation data against AB isolates using lead aryl 2-AI adjuvants 15b and 20a

| *A. baumannii* strain | CLR MIC (μg/mL) + 15b (10 μM) | CLR MIC (μg/mL) + 20a (7.5 μM) |
|---|---|---|
| 5711 | 4 | 1 |
| 8967 | 1 | 0.25 |

We had reported that compounds 1 and 2 antagonize the activity of the polymyxin colistin against A1B5075, effecting an increase in colistin MIC from 1 to 4 μg/mL at 30 μM. The mechanism of action of colistin is well-documented, and it is known that binding to LPS plays a significant role in polymyxin activity. In addition, a genome sequencing study of some colistin resistant strains of *A. baumannii*, revealed that loss of LPS imparts increased colistin resistance. It was posited that adjuvants 1 and 2 could be interfering with LPS production or assembly and thus affecting the ability of colistin to bind to its target. Therefore, we wanted to evaluate the effect of these second-generation adjuvants at their active concentrations on colistin activity against AB5075 (Table 6). Some compounds that display moderate CLR potentiation at 30 μM, such as compounds 4h, 4m, or 4u, did not potentiate nor antagonize colistin activity when dosed at 30 μM (Table 6). However, the most active compounds from the CLR potentiation screenings did increase the MIC of colistin by two- to eight-fold when dosed at their active concentrations against AB5075 (Table 6), as seen with adjuvants 1 and 2.

TABLE 6

Dose-response of active aryl tails for colistin potentiation against AB5075.

| Compound | Concentration Tested (μM) | Colistin MIC (μg/mL) |
|---|---|---|
| — | — | 0.5 |
| 4h | 30 | 0.5 |
| 4i | 30 | 1 |
| 4k | 30 | 1 |
| 4m | 30 | 0.5 |
| 4n | 7.5 | 1 |
| 4o | 15 | 1 |
| 4p | 15 | 1 |
| | 10 | 0.5 |
| 4r | 30 | 4 |
| 4s | 30 | 0.25 |
| 4u | 30 | 0.5 |
| 4v | 30 | 1 |
| 4y | 30 | 4 |
| | 20 | 4 |
| | 10 | 4 |
| 6a | 30 | 1 |
| | 20 | 0.5 |
| 6b | 30 | 4 |
| | 20 | 1 |
| 10a | 30 | 1 |
| | 20 | 0.5 |
| 10d | 30 | 8 |
| | 20 | 2 |
| | 10 | 1 |
| 10e | 30 | 4 |
| | 20 | 1 |
| 15a | 30 | 4 |
| 15b | 30 | 8 |
| | 20 | 8 |
| | 10 | 2 |
| 17a | 15 | 2 |
| 17b | 15 | 2 |
| 20a | 15 | 4 |
| | 7.5 | 0.5 |

TABLE 6-continued

Dose-response of active aryl tails for colistin potentiation against AB5075.

| Compound | Concentration Tested (μM) | Colistin MIC (μg/mL) |
|---|---|---|
| 20b | 7.5 | 1 |
| 20c | 30 | 4 |

Finally, parent adjuvant 1 was evaluated for its ability to suppress the evolution of CLR resistance in AB5075 in comparison to that occurring upon exposure to CLR alone over the course of nine consecutive days. Evaluation of resistance evolution was conducted by serially passaging AB5075 in the presence of CLR with and without adjuvant 1 and determining CLR MICs of the resultant bacterial populations. When exposed to CLR alone, after day 2 of the evolution assay, the MIC of CLR increased from 32 μg/mL to ≥128 μg/mL in AB5075 (Table 7). By day 6 of serial exposure, the MIC of CLR had risen to 512 μg/mL, and the MIC of CLR remained approximately 512 μg/mL throughout the remaining three days of the assay (Table 7). We then tested whether adjuvant 1 could reduce the MIC of this mutant. At 30 μM, compound 1 reduced the CLR MIC from 512 to 2 μg/mL, demonstrating that the adjuvant was still active against a more CLR resistant strain.

TABLE 7

CLR potentiation data for the evolution assay using CLR-alone exposure to AB5075 over the course of nine consecutive days.

| Day | CLR MIC (μg/mL) |
|---|---|
| 0 | 32 |
| 2 | ≥128 |
| 4 | 128 |
| 6 | 512 |
| 8 | 512 |

TABLE 8

CLR potentiation data with parent compound 1 for the evolution assay using serial passage of CLR-adjuvant 1 (at 30 μM) to AB5075 over the course of nine consecutive days.

| Day | Compound 1 Concentration Tested (μM) | CLR MIC (μg/mL) |
|---|---|---|
| 2 | 0 | 16 |
| | 30 | 0.25 |
| 4 | 0 | 32 |
| | 30 | 0.25 |
| 6 | 0 | 32 |
| | 30 | 0.25 |
| 8 | 0 | 32 |
| | 30 | ≤0.5 |
| 10 | 0 | 32 |
| | 30 | 0.25 |

The evolution assay was next conducted via serial passaging of AB5075 in the presence of CLR and 30 μM of adjuvant 1. We observed that adjuvant 1 suppressed the increase in macrolide resistance in AB5075 (Table 8) throughout the entire nine-day course. On day 2 and day 9 of passaging, the CLR MIC remained unchanged at 32 μg/mL, and the combination of adjuvant 1 at 30 μM lowered the CLR MIC 128-fold to 0.25 μg/mL, identical to what we observe for the activity of 1 against the parent AB5075 (Table 8).

In summary, we report optimized adjuvants within the aryl 2-AI class for macrolide potentiation against a virulent strain of gram-negative bacteria, AB5075 (Scheme 7). Compounds 4o, 4p, 4r, and 17b retained significant adjuvant activity at 10 μM, lowering the MIC of CLR 16-, 32-, eight-, and 16-fold, respectively, which was comparable to the 16-fold reduction at 10 μM for original adjuvants 1 and 2. Adjuvants that surpassed the activity of 1 and 2 were the amide-linked derivatives 4y, 10d, 15b as well as urea analogs 20a-c. At 10 μM, compound 4y reduced the MIC of CLR by 128-fold, where compounds 10d and 15b reduced the MIC of CLR by 64-fold at 10 μM. However, compounds 10d and 15b both surpassed compound 4y's activity at 7.5 μM, lowering the MIC of CLR by eight- and 32-fold, respectively.

The urea analog 20c, exhibited comparable adjuvant activity as amide compounds 10d and 15b at 7.5 μM, lowering the MIC of CLR by 16-fold. Interestingly, compound 20c was able to lower the MIC of CLR to ≤0.0625 μg/mL when dosed at higher concentrations (≥20 μM), which surpassed the fold reductions seen thus far with CLR. Urea derivatives 20a and 20b were more toxic, displaying standalone MIC values of 50 and 25 μM; however, they maintained the highest adjuvant activity at 7.5 μM out of all of the screened compounds. Compound 20a lowered the MIC of CLR 128-fold from 32 to 0.25 μg/mL at 7.5 μM, and compound 20b lowered the MIC of CLR 64-fold to 0.5 μg/mL at 7.5 μM.

Lead adjuvants 15b and 20a potentiated CLR activity against 23 additional clinically relevant *A. baumannii* strains at 10 and 7.5 μM, respectively. An evolution assay indicated that original adjuvant 1 suppresses the acquisition of CLR resistance in AB5075. Overall, these compounds represent valuable tools in ongoing mechanism of action studies, as well as future murine model studies to determine whether these compounds can potentiate CLR in vivo.

Scheme 7. Structure-activity relationship trends observed and representative clarithromycin potentiation results against AB5075

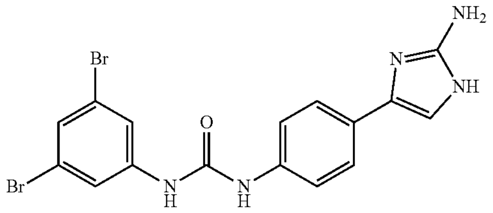

20a
CLR MIC + 7.5 μM = 0.25 μg/mL
CLR MIC + 5 μM = 4 μg/mL tail + linker modification core modification tail modification

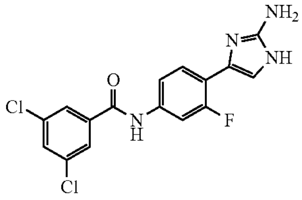

10d
CLR MIC + 10 μM= 0.5 μg/mL
CLR MIC + 7.5 μM = 4 μg/mL

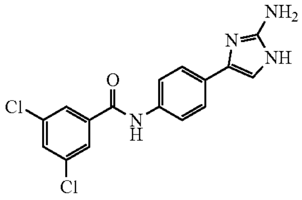

1
CLR MIC + 10 μM= 2 μg/mL

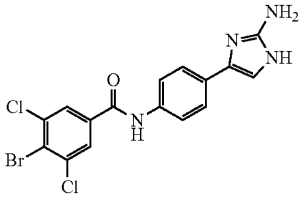

4y
CLR MIC + 10 μM= 0.25 μg/mL tail + core modification

-continued

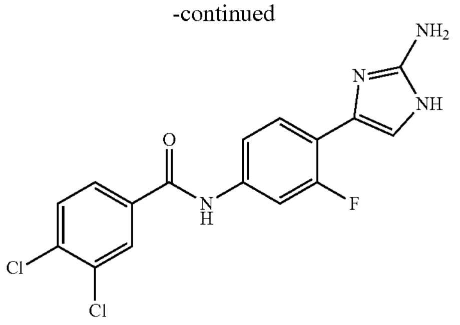

15b
CLR MIC + 10 μM= 0.5 μg/mL
CLR MIC + 7.5 μM = 1 μg/mL

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard- or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.10% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. Nos. 4,992,478 (Geria), 4,820,508 (Wortzman), 4,608,392 (Jacquet et al.), and 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 $mg/m^2$, conveniently 10 to 750 $mg/m^2$, most conveniently, 50 to 500 $mg/m^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention provides therapeutic methods of treating infections in a mammal, which involve administering to a mammal having an infection an effective amount of a compound or composition described herein. A mammal includes a primate, human, rodent, canine, feline, bovine, ovine, equine, swine, caprine, bovine and the like.

The ability of a compound of the invention to treat infections may be determined by using assays well known to the art. For example, the design of treatment protocols, toxicity evaluation, data analysis, and quantification of bacterium kill, are known. In addition, ability of a compound to treat infections may be determined using the tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Biology Experimental

Bacterial Strains and Antimicrobial Agents. *Acinetobacter baumannii* clinical isolate 5075 was obtained from Dr. Colin Manoil at the University of Washington. Colonies were grown on lysogeny broth (LB) agar. Cation-adjusted Mueller-Hinton Broth (CAMHB) (catalog number 212322) were purchased from BD Diagnostics. LB broth was purchased from Fisher Scientific (catalog number BP9722-2). Clarithromycin (catalog number C2220) was purchased from TCI. Colistin sulfate salt (catalog number C4461) was purchased from Sigma Aldrich. All assays were completed in duplicate and repeated at least two separate times. All compounds were dissolved as their HCl salts in molecular biology grade DMSO as 10 or 100 mM stock solutions and stored at −20° C. Colistin was dissolved in sterile water while clarithromycin was dissolved in molecular biology grade DMSO.

Broth microdilution method for MIC determination. Day cultures (6 h) of each bacterial strain in cation adjusted Mueller Hinton II broth (CAMHB, Fisher Scientific U.S.) were subcultured to $5\times10^5$ CFU/mL in CAMHB. Aliquots (1 mL) were placed in culture tubes and compound was added from 10 mM stock samples in DMSO, such that compound concentration equaled highest concentration tested (200 μM). Samples were then aliquoted (200 μL) into the first wells of a 96-well plate, with all remaining wells being filled with 100 μL of initial bacterial subculture. Row one wells were mixed five times, before 100 μL was transferred to row two. Row two was then mixed five times, and 100 μL was transferred to row three. This process was repeated until the final row had been mixed; this served to serially dilute the compound. Plates were then covered with GLAD Press n'Seal and incubated under stationary conditions at 37° C. for 16 h. MIC values were then recorded as the lowest concentration at which no bacterial growth was observed.

Broth microdilution method for antibiotic potentiation. Day cultures (6 h) of bacteria in CAMHB were subcultured to $5\times10^5$ CFU/mL in CAMHB. Aliquots (4 mL) were placed in culture tubes and dosed with compound from 10 mM stock samples to give the desired concentration of the compound to be tested against the particular bacterial strain; this insured non-toxic DMSO concentrations ≤0.3% in each well. 1 mL of the resulting solution was placed in a separate culture and dosed with antibiotic at the highest concentration to be tested. Bacteria treated with antibiotic alone served as the control. Row one of a 96-well plate was filled with 200 μL of the antibiotic/2-AI solution, and rows 2-12 were filled with 100 μL each of the remaining 4 mL of bacterial subculture containing adjuvant at the desired concentration, except for the control lane which contained only bacterial subculture. Row one was then mixed five times, and 100 μL was transferred to row two, which was then mixed five times before being transferred to row three. This process was repeated until all rows had been mixed, except for row twelve which would have only 2-AI to serve as a control to monitor potential toxicity. The 96-well plate was then covered in Glad Press n'Seal and incubated under stationary conditions at 37° C. for 16 h. MIC values were determined as the lowest concentration at which no bacterial growth was observed, and fold reductions were determined by comparison to antibiotic control lane.

Dose-response of Adjuvant Assay. The procedure for 'broth microdilution method for antibiotic potentiation' was followed using 4 mL aliquots of adjuvant at various concentrations: 0, 5, 7.5, 10, 15, 20, 25, and 30 μM.

Evolution of Clarithromycin Resistance in *A. baumannii. A. baumannii* 5075 was grown in CAMHB overnight then subcultured ($5\times10^5$ CFU/mL) in 6 mL of fresh CAMHB. Adjuvant was added into this 6-mL subculture at either 10 or 30 μM concentrations. Aliquots of 1 mL were taken and placed into five individual culture tubes and clarithromycin was added at concentrations of 2- and 4-fold MIC greater than and also 2- and 4-fold less than reported clarithromycin MIC values with adjuvant, with the middle tube representing the clarithromycin MIC value. After 24 h of shaking at 37° C., bacterial growth was evaluated and the highest clarithromycin concentration with growth was carried forward and MICs determined every two days. This was serially repeated for a period of nine days.

Example 2. Chemistry Experimental

All reagents used for chemical synthesis were purchased from commercially available sources (VWR U.S., Fisher Scientific U.S., or Sigma Aldrich U.S.) and used without further purification. Flash chromatography was performed using 60 Å mesh standard grade silica gel from Sorbetch. NMR solvents were obtained from Cambridge Isotope Labs and used as is. All $^1$H NMR (400 or 500 MHz) were recorded at 25° C. on Bruker AVANCE III HD spectrometers. All $^{13}$C NMR (100 or 125 MHz) spectra were recorded at 25° C. on Bruker AVANCE III HD spectrometers. Chemical shifts (δ) are given in parts per million (ppm) relative to the respective NMR solvent; coupling constants (J) are in hertz (Hz). Abbreviations used are s, singlet; bs, broad singlet; d, doublet; dd, doublet of doublets; t, triplet; dt, doublet of triplets; tt, triplet of triplets; m, multiplet. High-resolution mass spectrometry measurements were obtained at either Notre Dame Department of Chemistry Mass Spectrometry and Proteomics Facility, or in part by the Molecular Education, Technology and Research Innovation Center (METRIC) at NC State University, which is supported by the State of North Carolina. Infrared spectra were obtained on a Bruker Alpha II FTIR spectrophotometer ($\nu_{max}$ in $cm^{-1}$). UV absorbance was recorded on a Genesys 10 scanning UV/visible spectrophotometer ($\lambda_{max}$ in nm). The purities of the tested compounds were all verified to be ≥95% by LC-MS analysis on an Advion LC-MS 2020 with Kinetex, 2.6 mm, C18 50×2.10 mm.

General procedure for alloc protection. The corresponding aniline (17 mmol, 1 eq) was dissolved in a 1:1 ratio of $H_2O$:1,4-dioxane (45 mL:45 mL) at room temperature. DIPEA (33 mmol, 2 eq) and $NaHCO_3$ (50 mmol, 3 eq) were added to the reaction mixture. The reaction mixture was cooled to 0° C. and allyl chloroformate (17 mmol, 1 eq) was added dropwise to the reaction mixture, and the reaction was allowed to stir for 16 h. Upon completion, the reaction mixture was cooled to 0° C. and quenched with 1N HCl (70 mL), at which point white solid crashed out of solution. The precipitate was vacuum filtered and collected as desired aniline product.

General procedure for saponification. Methyl ester analogs (1 eq, 1.34 mmol) were dissolved in a 1:1 mixture of MeOH:$H_2O$ (16 mL) to which a 5 M solution of sodium hydroxide (4 mL) was added at room temperature. The reaction solution was stirred for 3 h. After completion, the MeOH was removed under reduced pressure. The remaining aqueous solution was cooled to 0° C., and 12 N HCl was added until the pH reached ~2. The resulting precipitate was then isolated using vacuum filtration and allowed to dry under high vacuum for 2 h.

General procedure for acid chloride formation. To a solution of anhydrous DCM (20 mL) was added the benzoic acid analogs (1 eq, 5.1 mmol), followed by the dropwise addition of commercially available oxalyl chloride (1.1 eq, 5.6 mmol) and catalytic amount of DMAP (0.01 eq, 0.05 mmol) at 0° C. The reaction was stirred at 0° C. for 1 h, then solvent was removed under reduced pressure and the crude was allowed to dry under high vacuum for 0.5 h and immediately used in the general procedure for α-bromo-ketone production.

General procedure for α-bromo-ketone production. In a flame dried round bottom under $N_2$ atmosphere was added the corresponding alloc-protected benzoic acid (6.0 mmol, 1 eq) dissolved in anhydrous DCM (20 mL). The reaction mixture was cooled to 0° C. and oxalyl chloride (6.6 mmol, 1.1 eq) was added dropwise followed by the addition of a catalytic amount of DMF (6.5 μmol, 0.0001 eq). The reaction mixture was allowed to stir for 2 h, at which point the solution was concentrated under reduced pressure to yield corresponding desired acid chloride. The acid chloride product (10 mmol, 1 eq) was dissolved in anhydrous DCM (20 mL) and added dropwise to a distilled solution of diazomethane (50 mmol, 5 eq) in ether at 0° C. and stirred for 1.5 h. TLC analysis was used to verify consumption of acid chloride starting material, at which point concentrated HBr (50 mmol, 5 eq) was added dropwise at 0° C. and stirred an additional 30 min. Upon reaction completion via TLC analysis, the reaction solution was quenched with $NaHCO_3$ (200 mL) and the reaction was extracted with DCM (3×300 mL). The combined organic layers were rinsed with brine (1×30 mL) and dried with $MgSO_4$. The solvent was removed under reduced pressure, and the residue was rinsed three times with $Et_2O$ to remove undesired impurities. The remaining residue was collected and dried on high vacuum as the corresponding desired α-bromo-ketone and used without further purification in the 'general procedure for Boc-guanidine cyclization'.

General procedure for Boc-guanidine cyclization. The corresponding α-bromo-ketone (2 mmol, 1 eq) and boc-guanidine (6 mmol, 3 eq) were dissolved in anhydrous THF (20 mL) and stirred for 3 h at 56° C. The reaction solvent was removed under reduced pressure to yield a crude residue. The crude residue was purified by flash chromatography (5-100% EtOAc/hexanes) to afford desired 2-amino-imidazole compounds.

General procedure for alloc deprotection. The corresponding alloc-protected compound (1.5 mmol, 1 eq) was dissolved in 200-proof EtOH (20 mL). Next, the reaction solution was cooled to 0° C. and tetrakis(triphenylphosphine)palladium (0) (0.035 mmol, 0.02 eq) and sodium borohydride (3.0 mmol, 2 eq) were added to the reaction mixture and allowed to stir for 4 h. After completion, the reaction was extracted with EtOAc (2×30 mL) and washed with deionized water (10 mL). The combined organic layers were rinsed with brine (10 mL) and dried with $MgSO_4$, then concentrated under reduced pressure. The residue was then purified using flash chromatography (30% EtOAc in hexanes) to yield the corresponding aniline product.

General procedure for amide formation. To a solution of anhydrous THF (10 mL) was added the aniline intermediate (1 eq, 1.20 mmol) and $K_3PO_4$ (1.5 eq, 1.79 mmol) at 0° C., followed by the dropwise addition of commercially available 3,5-dichlorobenzoyl chloride (1 eq, 1.20 mmol). The reaction was warmed to room temperature and stirred for 16 h. Water (10 mL) was added to the reaction solution and the desired product was extracted with EtOAc (3×30 mL), followed by the organic layers being rinsed with brine (2×10 mL). The organic layers were combined and dried with $MgSO_4$, then concentrated under reduced pressure. Final product was purified using flash chromatography (0-50% EtOAc in hexanes).

General procedure for amide formation using EDC coupling. A solution of commercially available carboxylic acid (4.4 mmol, 1.5 eq), EDC (17.7 mmol, 6 eq), DMAP (1.5 mmol, 0.5 eq), and commercially available aniline (3.0 mmol, 1 eq) was made in anhydrous DCM (50 mL). The reaction was refluxed at 40° C. under an atmosphere of nitrogen and allowed to stir for 16 h at room temperature. After completion, the reaction was allowed to cool to room temperature and water (30 mL) was added to the flask. The desired product was extracted with DCM (3×50 mL), washed with 1N HCl (2×20 mL), then rinsed with brine (2×20 mL). The organic layers were combined and dried with $MgSO_4$, then concentrated under reduced pressure. Final product was purified using flash chromatography (0-50% EtOAc in hexanes).

General procedure for Boc deprotection. The corresponding Boc-protected 2-AI (1.3 mmol, 1 eq) was dissolved in DCM (1 mL) and TFA (2 mL) was added dropwise into the reaction vessel. The reaction was stirred at room temperature for 3 h. Once reaction reached completion via TLC analysis, the solvent was removed under reduced pressure. The resulting TFA salt was dissolved in MeOH (10 mL) then spiked with 6 M HCl (0.5 mL) and solvent was removed to yield their corresponding HCl salts.

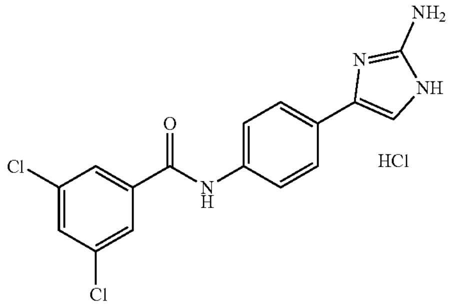 [SMILES: Nc1nc(-c2ccc(NC(=O)c3cc(Cl)cc(Cl)c3)cc2)c[nH]1 ; Cl]

N-(4-(2-amino-1H-imidazol-4-yl)phenyl)-3,5-dichlorobenzamide hydrochloride (1): Compound 1 was prepared following a previously published protocol to obtained as a white solid in 64% yield (*J Med Chem* 2014, 57 (17), 7450). $^1H$ NMR (400 MHz, DMSO-$d_6$) δ 12.63 (s, 1H), 11.99 (s, 1H), 10.55 (s, 1H), 7.99 (d, J=1.9 Hz, 2H), 7.90 (t, J=1.9 Hz, 1H), 7.83 (d, J=8.7 Hz, 2H), 7.66 (d, J=8.7 Hz, 2H), 7.47 (bs, 2H), 7.36 (s, 1H).

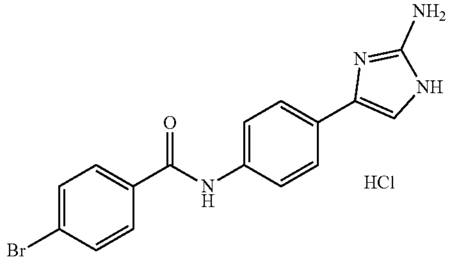 [SMILES: Nc1nc(-c2ccc(NC(=O)c3ccc(Br)cc3)cc2)c[nH]1 ; Cl]

N-(4-(2-amino-1H-imidazol-4-yl)phenyl)-4-bromobenzamide hydrochloride (4h): Compound 4h was prepared following said previously published protocol to obtained as a white solid in 72% yield. $^1H$ NMR (400 MHz, Methanol-$d_4$) δ 7.86 (d, J=8.6 Hz, 1H), 7.82 (d, J=8.8 Hz, 1H), 7.70 (d, J=8.5 Hz, 1H), 7.58 (d, J=8.7 Hz, 1H), 7.14 (s, 1H).

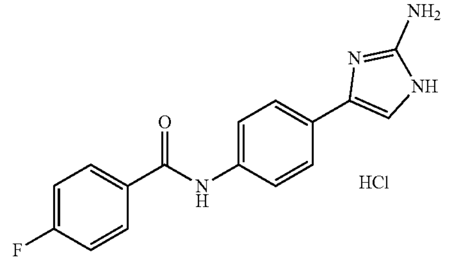 [SMILES: Nc1nc(-c2ccc(NC(=O)c3ccc(F)cc3)cc2)c[nH]1 ; Cl]

N-(4-(2-amino-1H-imidazol-4-yl)phenyl)-4-fluorobenzamide hydrochloride (4j): Compound 4j was prepared following the previously published protocol to obtained as a tan solid in 57% yield. $^1H$ NMR (400 MHz, DMSO-$d_6$) δ 12.84 (s, 1H), 12.08 (s, 1H), 10.44 (s, 1H), 8.06 (dd, J=8.7, 5.6 Hz, 2H), 7.86 (dd, J=8.8, 2.1 Hz, 2H), 7.65 (d, J=8.7 Hz, 2H), 7.46 (s, 2H), 7.38 (t, J=8.8 Hz, 2H), 7.34 (s, 1H).

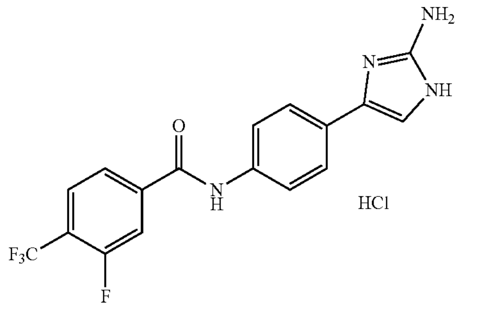 [SMILES: Nc1nc(-c2ccc(NC(=O)c3ccc(C(F)(F)F)c(F)c3)cc2)c[nH]1 ; Cl]

N-(4-(2-amino-1H-imidazol-4-yl)phenyl)-3-fluoro-4-(trifluoromethyl)benzamide hydrochloride (4p): Compound 4p was prepared following the previously published protocol to obtained as a tan solid in 36% yield. $^{1}H$ NMR (400 MHz, DMSO-$d_6$) δ 12.69 (s, 1H), 12.02 (s, 1H), 10.65 (s, 1H), 8.07 (d, J=11.4 Hz, 1H), 8.00 (d, J=5.9 Hz, 2H), 7.85 (d, J=8.8 Hz, 2H), 7.67 (d, J=8.7 Hz, 2H), 7.46 (bs, 2H), 7.36 (s, 1H).

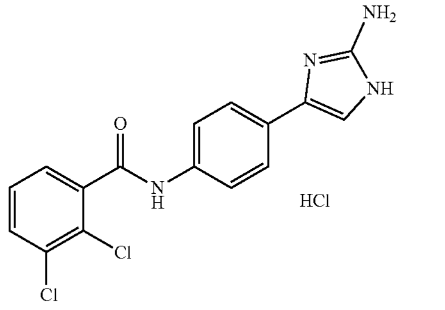 [SMILES: Nc1nc(-c2ccc(NC(=O)c3cccc(Cl)c3Cl)cc2)c[nH]1 ; Cl]

N-(4-(2-amino-1H-imidazol-4-yl)phenyl)-2,3-dichlorobenzamide hydrochloride (4q): Compound 4q was prepared following the previously published protocol to obtained as a tan solid in 55% yield. $^{1}H$ NMR (400 MHz, Methanol-$d_4$) δ 7.79 (d, J=8.8 Hz, 2H), 7.68 (dd, J=7.9, 1.7 Hz, 1H), 7.59 (d, J=8.7 Hz, 2H), 7.51 (dd, J=7.6, 1.7 Hz, 1H), 7.44 (t, J=7.8 Hz, 1H), 7.15 (s, 1H).

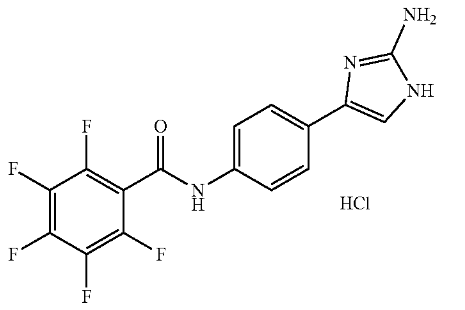 [SMILES: Nc1nc(-c2ccc(NC(=O)c3c(F)c(F)c(F)c(F)c3F)cc2)c[nH]1 ; Cl]

N-(4-(2-amino-1H-imidazol-4-yl)phenyl)-2,3,4,5,6-pentafluorobenzamide hydrochloride (4x): Compound 4x was prepared following the previously published protocol to obtained as a tan solid in 61% yield. $^{1}H$ NMR (400 MHz, DMSO-$d_6$) δ 12.77 (s, 1H), 12.07 (s, 1H), 11.21 (s, 1H), 7.83-7.60 (m, 4H), 7.47 (bs, 2H), 7.37 (s, 1H).

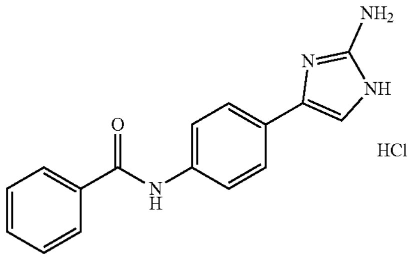 [SMILES: Nc1nc(-c2ccc(NC(=O)c3ccccc3)cc2)c[nH]1 ; Cl]

N-(4-(2-amino-1H-imidazol-4-yl)phenyl)benzamide hydrochloride (4a): To a solution of anhydrous DCM (5 mL) was added the aniline intermediate 3 (1 eq, 0.23 mmol) and trimethylamine (3 eq, 0.72 mmol) at room temperature, followed by the dropwise addition of commercially available benzoyl chloride (1.7 eq, 0.39 mmol). The reaction was stirred at 25° C. for 16 h. The reaction solution was washed with water (2×10 mL) and the desired product was extracted with DCM (2×20 mL), followed by the organic layers being rinsed with brine (2×10 mL). The organic layers were combined and dried with $MgSO_4$, then concentrated under reduced pressure. The crude material was purified using flash chromatography (0-15% EtOAc in hexanes). After purification, the general procedure for Boc deprotection was utilized to obtain 4a as a tan solid in 40% yield. $^{1}H$ NMR (400 MHz, Methanol-$d_4$) δ 7.99-7.92 (m, 2H), 7.87-7.81 (m, 2H), 7.64-7.49 (m, 5H), 7.14 (s, 1H). $^{13}C$ NMR (101 MHz, Methanol-$d_4$) δ 168.9, 149.3, 140.4, 136.1, 133.1, 129.7, 128.9, 128.7, 126.1, 124.9, 122.5, 109.5. UV (λmax nm): 312; IR ($\nu_{max}$ $cm^{-1}$) 3259, 3134, 3027, 1676, 1641, 1447; HRMS (ESI) calcd for $C_{16}H_{15}N_4O$ $[M+H]^+$: 279.1240, found: 279.1234.

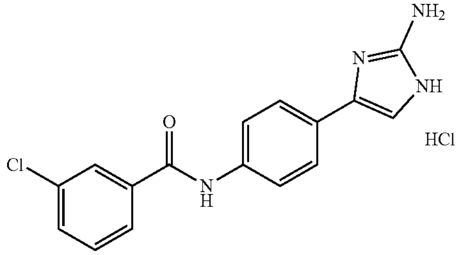 [SMILES: Nc1nc(-c2ccc(NC(=O)c3cccc(Cl)c3)cc2)c[nH]1 ; Cl]

4-(2-Amino-3H-imidazol-4-yl)phenyl]-3-chlorobenzamide hydrochloride (4d): To a solution of anhydrous THF (5 mL) was added the aniline intermediate 3 (1 eq, 0.20 mmol) and triethylamine (1 eq, 0.20 mmol) at −78° C., followed by the dropwise addition of commercially available 3-chlorobenzoyl chloride (1 eq, 0.20 mmol). The resulting solution was then stirred at −78° C. for 0.5 h and quenched with MeOH (1 mL) before being concentrated under reduced pressure and purified by flash column chromatography (5-50% EtOAc/hexanes) to obtain 92 mg (75%) of the Boc-protected 2-AI product a white solid. After purification, the general procedure for Boc deprotection was utilized to obtain 4d as a tan solid in 95% yield. $^{1}H$ NMR (400 MHz, Methanol-$d_4$) δ 7.94 (t, J=1.9 Hz, 1H), 7.87 (d, J=7.6, Hz, 1H), 7.83-7.78 (m, 2H), 7.61-7.54 (m, 3H), 7.50 (t, J=7.9 Hz, 1H), 7.12 (s, 1H). $^{13}C$ NMR (101 MHz, Methanol-$d_4$) δ 165.7, 147.8, 138.6, 136.6, 134.3, 131.5, 129.9, 127.4, 127.3, 125.7, 124.6, 123.6, 121.0, 108; HRMS (ESI) calcd for $C_{16}H_{14}ClN_4O$ $[M+H]^+$: 313.0851, found: 313.0846.

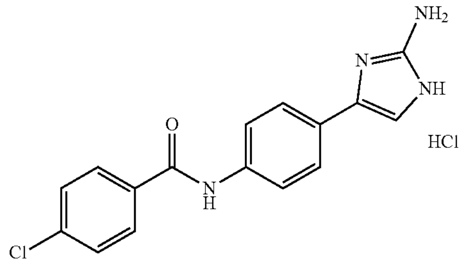 [SMILES: Nc1nc(-c2ccc(NC(=O)c3ccc(Cl)cc3)cc2)c[nH]1 ; Cl]

4-(2-Amino-3H-imidazol-4-yl)phenyl]-4-chlorobenzamide hydrochloride (4i): The above compound was synthesized in a similar manner to compound 4d, followed by using the general procedure for Boc deprotection to obtain 4i as a white solid in 97% yield. $^1$H NMR (400 MHz, Methanol-$d_4$) δ 7.92 (d, J=8.9 Hz, 2H), 7.83-7.78 (m, 1H), 7.60-7.55 (m, 4H), 7.55-7.50 (m, 1H), 7.13 (s, 1H). $^{13}$C NMR (101 MHz, Methanol-$d_4$) δ 166.2, 154.6, 138.8, 137.7, 133.3, 129.0, 128.4, 127.3, 124.7, 123.5, 121.0, 108.1; HRMS (ESI) calcd for $C_{16}H_{13}ClN_4O$ $[M+H]^+$: 313.0851, found 313.0852.

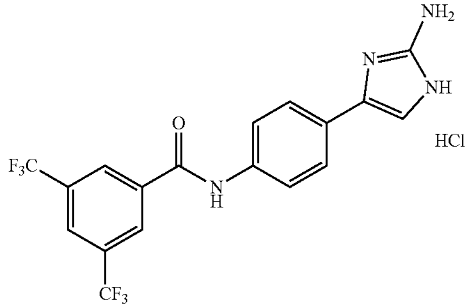 [SMILES: Nc1nc(-c2ccc(NC(=O)c3cc(C(F)(F)F)cc(C(F)(F)F)c3)cc2)c[nH]1 ; Cl]

4-(2-Amino-3H-imidazol-4-yl)phenyl]-3,5-(bistrifluoromethyl)benzamide hydrochloride (4l): The above compound was synthesized in a similar manner to compound 4d, followed by using the general procedure for Boc deprotection to obtain 4l as a white solid in 99% yield. $^1$H NMR (400 MHz, DMSO-$d_6$) δ 13.03 (s, 1H), 12.18 (s, 1H), 8.63 (s, 1H), 8.35 (s, 1H), 7.91-7.81 (m, 3H), 7.72-7.62 (m, 2H), 7.47 (s, 2H), 7.35 (d, J=1.3 Hz, 1H). $^{13}$C NMR (101 MHz, DMSO-$d_6$) δ 163.0, 148.1, 138.6, 138.5, 137.3, 131.1, 130.7, 130.4, 126.6, 125.1, 124.9, 124.1, 122.2, 121.3, 121.2, 109.4; HRMS (ESI) calcd for $C_8H_{12}F_6N_4O$ $[M+H]^+$: 415.0988, found 415.0988.

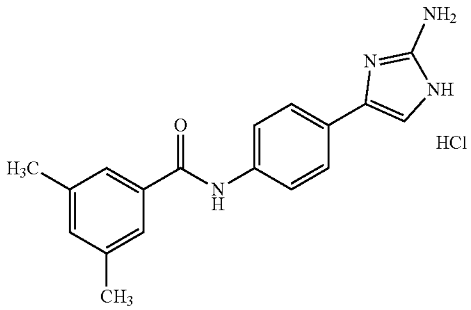 [SMILES: Cc1cc(C)cc(C(=O)Nc2ccc(-c3c[nH]c(N)n3)cc2)c1 ; Cl]

N-(4-(2-amino-1H-imidazol-4-yl)phenyl)-3,5-dimethylbenzamide hydrochloride (4m): The above compound was synthesized in a similar manner to compound 4a, followed by using the general procedure for Boc deprotection to obtain 4m as a tan solid in 94% yield. $^1$H NMR (400 MHz, Methanol-$d_4$) δ 7.82 (d, J=8.8 Hz, 2H), 7.60-7.53 (m, 4H), 7.25 (s, 1H), 7.14 (s, 1H), 2.40 (s, 6H). $^{13}$C NMR (101 MHz, Methanol-$d_4$) δ 169.3, 149.2, 140.4, 139.6, 136.0, 134.5, 128.9, 126.4, 126.1, 124.8, 122.4, 109.5, 21.3. UV (λmax nm): 312; IR ($\nu_{max}$ $cm^{-1}$) 3260, 3134, 3005, 2917, 2744, 1673, 1515; HRMS (ESI) calcd for $C_{18}H_{19}N_4O$ $[M+H]^+$: 307.1553, found: 307.1534.

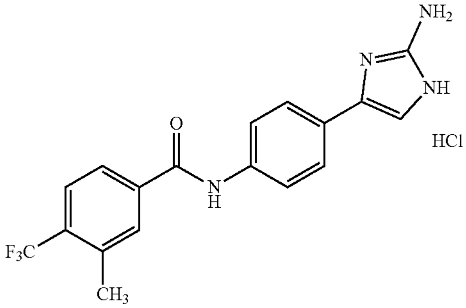 [SMILES: Cc1cc(C(=O)Nc2ccc(-c3c[nH]c(N)n3)cc2)ccc1C(F)(F)F ; Cl]

4-(2-Amino-3H-imidazol-4-yl)phenyl]-3-chloro-4-(trifluoromethyl)benzamide hydrochloride (4n): The above compound was synthesized in a similar manner to compound 4d, followed by using the general procedure for Boc deprotection to obtain 4n as a tan solid in 98% yield. $^1$H NMR (400 MHz, Methanol-$d_4$) δ 8.15 (d, J=1.6 Hz, 1H), 8.06-7.97 (m, 1H), 7.92 (d, J=8.2 Hz, 1H), 7.87-7.78 (m, 2H), 7.61-7.54 (m, 2H), 7.14 (s, 1H). $^{13}$C NMR (101 MHz, Methanol-$d_4$) δ 164.2, 147.8, 139.8, 138.4, 130.4, 127.8, 127.7, 127.2, 126.2, 124.7, 124.0, 123.8, 121.0, 108.2; HRMS (ESI) calcd for $C_{17}H_{12}ClF_3N_4O$ $[M+H]^+$: 381.0728, found 381.0715.

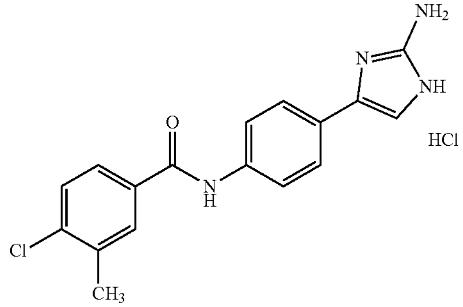 [SMILES: Cc1cc(C(=O)Nc2ccc(-c3c[nH]c(N)n3)cc2)ccc1Cl ; Cl]

4-(2-Amino-3H-imidazol-4-yl)phenyl]-3-(trifluoromethyl)-4-chlorobenzamide hydrochloride (4o): The above compound was synthesized in a similar manner to compound 4d, followed by using the general procedure for Boc deprotection to obtain 4o as a yellow solid in 95% yield. $^1$H NMR (400 MHz, Methanol-$d_4$) δ 8.37-8.32 (m, 1H), 8.21-8.15 (m, 1H), 7.86-7.80 (m, 1H), 7.77 (d, J=8.3 Hz, 2H), 7.61-7.54 (m, 2H), 7.15 (d, J=8.2 Hz, 1H). $^{13}$C NMR (101 MHz, Methanol-$d_4$) δ 164.5, 147.8, 138.5, 135.1, 133.9, 132.3, 131.7, 127.3, 126.8, 126.8, 124.6, 123.7, 121.0, 108.2; HRMS (ESI) calcd for $C_{17}H_{12}ClF_3N_4O$ $(M^+)$ 381.0728, found 381.0725.

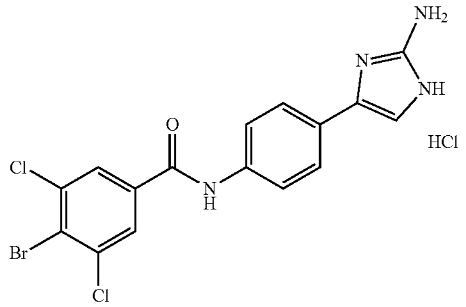 [SMILES: Nc1nc(-c2ccc(NC(=O)c3cc(Cl)c(Br)c(Cl)c3)cc2)c[nH]1 ; Cl]

N-(4-(2-amino-1H-imidazol-4-yl)phenyl)-4-bromo-3,5-dichlorobenzamide hydrochloride (4y): The above compound was synthesized in a similar manner to compound 4a, followed by using the general procedure for Boc deprotection to obtain 4y as a tan solid in 11% yield. $^1$H NMR (400 MHz, Methanol-d$_4$) δ 8.08 (s, 2H), 7.83 (d, J=8.8 Hz, 2H), 7.58 (d, J=8.8 Hz, 2H), 7.15 (s, 1H). $^{13}$C NMR (101 MHz, DMSO-d$_6$) δ 162.2, 147.6, 138.3, 135.7, 135.5, 128.0, 126.2, 126.1, 124.7, 123.6, 120.7, 109.0. UV (λmax nm): 330; IR ($\nu_{max}$ cm$^{-1}$) 3238, 3217, 3149, 3034, 1683, 1518; HRMS (ESI) calcd for $C_{16}H_{12}BrCl_2N_4O$ [M+H]$^+$: 424.9566, found: 424.9566.

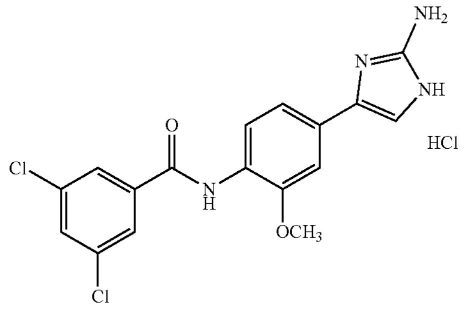 [SMILES: COc1cc(-c2c[nH]c(N)n2)ccc1NC(=O)c1cc(Cl)cc(Cl)c1 ; Cl]

N-(4-(2-amino-1H-imidazol-4-yl)-2-methoxyphenyl)-3,5-dichlorobenzamide hydrochloride (6a): To a solution of anhydrous DCM (20 mL) was added the benzoic acid analog 5a (1 eq, 5.1 mmol), followed by the dropwise addition of commercially available oxalyl chloride (1.1 eq, 5.6 mmol) and catalytic amount of DMAP (0.01 eq, 0.05 mmol) at 0° C. The reaction was stirred at 0° C. for 1 h, then solvent was removed under reduced pressure and the crude was allowed to dry under high vacuum for 0.5 h and immediately used in the general procedure for α-bromo-ketone production. The corresponding α-bromo-ketone was obtained as a white solid in 63% yield. The corresponding α-bromo-ketone was used in the general procedure for Boc-guanidine cyclization to obtain the corresponding mono-Boc-protected 2-amino-imidazole as a green solid in 92% yield. To a solution of anhydrous THF (10 mL) and 10% Pd/C (0.040 g) was charged the mono-Boc-protected 2-aminoimidazole. Air was removed from the system, and the reaction was back flushed with hydrogen. This process was repeated three times before the reaction was placed under a hydrogen balloon at room temperature for 16 h. After that time, the reaction was filtered to remove the catalyst. The filtrate was concentrated under reduced pressure and corresponding aniline product was obtained in 100% yield as an orange solid. To a solution of anhydrous THF (10 mL) was added the aniline intermediate (1 eq, 1.20 mmol) and $K_3PO_4$ (1.5 eq, 1.79 mmol) at 0° C., followed by the dropwise addition of commercially available 3,5-dichlorobenzoyl chloride (0.9 eq, 1.08 mmol). The reaction was warmed to room temperature and stirred for 16 h. Water (10 mL) was added to the reaction solution and the desired product was extracted with EtOAc (3×30 mL), followed by the organic layers being rinsed with brine (2×10 mL). The organic layers were combined and dried with $MgSO_4$, then concentrated under reduced pressure. The crude material was purified using flash chromatography (0-50% EtOAc in hexanes). After purification, the general procedure for Boc deprotection was utilized to obtain 6a as a tan solid in 95% yield. $^1$H NMR (400 MHz, Methanol-d$_4$) δ 8.03 (d, J=8.3 Hz, 1H), 7.89 (d, J=1.9 Hz, 2H), 7.70 (t, J=1.9 Hz, 1H), 7.30 (d, J=1.9 Hz, 1H), 7.23 (s, 1H), 7.20 (dd, J=8.3, 1.9 Hz, 1H), 3.99 (s, 3H). $^{13}$C NMR (101 MHz, DMSO-d$_6$) δ 162.7, 152.3, 147.6, 137.6, 134.4, 131.0, 126.5, 126.3, 125.9, 125.8, 125.5, 116.0, 109.7, 107.8, 56.2. UV (λmax nm): 320; IR ($\nu_{max}$ cm$^{-1}$) 3416, 3261, 3064, 3009, 2958, 2776, 2549, 1681, 1634, 1285, 1225, 768; HRMS (ESI) calcd for $C_{17}H_{15}C_{12}N_4O_2$ [M+H]$^+$: 377.0567, found: 377.0561.

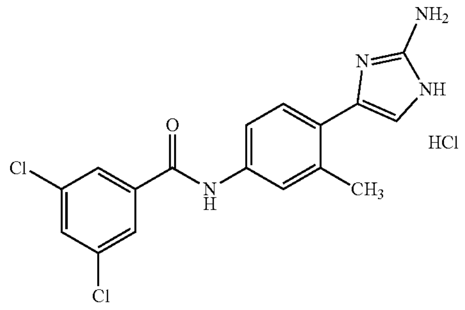 [SMILES: Cc1cc(NC(=O)c2cc(Cl)cc(Cl)c2)ccc1-c1c[nH]c(N)n1 ; Cl]

N-(4-(2-amino-1H-imidazol-4-yl)-3-methylphenyl)-3,5-dichlorobenzamide hydrochloride (6b): The above compound was synthesized in a similar manner to compound 6a, followed by using the general procedure for Boc deprotection to obtain 6b as a white solid in 93% yield. $^1$H NMR (400 MHz, DMSO-d$_6$) δ 12.48 (bs, 1H), 12.18 (bs, 1H), 10.54 (s, 1H), 8.01 (d, J=2.0 Hz, 2H), 7.89 (t, J=1.9 Hz, 1H), 7.77-7.69 (m, 2H), 7.49-7.34 (m, 3H), 7.02 (s, 1H), 2.38 (s, 3H). $^{13}$C NMR (101 MHz, DMSO-d$_6$) δ 162.8, 147.2, 138.6, 137.9, 135.9, 134.4, 131.1, 128.4, 126.6, 124.9, 123.0, 122.5, 118.0, 111.1, 21.1. UV (λmax nm): 224; IR ($\nu_{max}$ cm$^{-1}$) 3239, 3138, 3077, 2960, 2760, 1680, 1512, 708; HRMS (ESI) calcd for $C_{17}H_{15}Cl_2N_4O$ [M+H]$^+$: 361.0617, found: 361.0627.

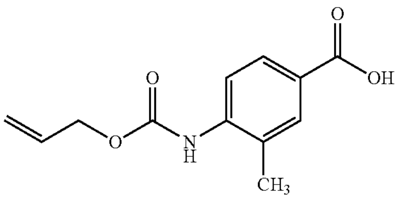 [SMILES: C=CCOC(=O)Nc1ccc(C(=O)O)cc1C]

4-(((allyloxy)carbonyl)amino)-3-methylbenzoic acid (8a): Using the general procedure for alloc protection, compound 8a was obtained as a white solid in 91% yield. $^1$H NMR (500 MHz, Chloroform-d) δ 11.18 (s, 1H), 8.11 (d, J=8.6 Hz, 1H), 7.98 (dd, J=8.6, 2.1 Hz, 1H), 7.91 (d, J=1.3 Hz, 1H), 6.72 (s, 1H), 5.99 (ddt, J=17.1, 10.4, 5.9 Hz, 1H), 5.40 (dq, J=17.2, 1.5 Hz, 1H), 5.30 (dq, J=10.4, 1.2 Hz, 1H), 4.71 (dt, J=5.9, 1.4 Hz, 2H), 2.31 (s, 3H). $^{13}$C NMR (126 MHz, Methanol-$d_4$) δ 169.6, 156.0, 142.2, 134.1, 133.1, 129.2, 127.5, 123.3, 118.1, 118.1, 66.9, 18.0. UV (λmax nm): 268; IR ($\nu_{max}$ cm$^{-1}$) 3287, 3089, 2966, 2872, 2663, 2545, 1685, 1241; HRMS (ESI) calcd for $C_{12}H_{12}NO_4$ [M−H]$^+$: 234.0772, found: 234.0776.

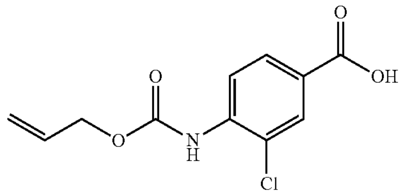 [SMILES: C=CCOC(=O)Nc1ccc(C(=O)O)cc1Cl]

4-(((allyloxy)carbonyl)amino)-3-chlorobenzoic acid (8b): Using the general procedure for alloc protection, compound 8b was obtained as a white solid in 92% yield. $^1$H NMR (500 MHz, Chloroform-d) δ 11.74 (s, 1H), 8.36 (d, J=8.7 Hz, 1H), 8.12 (d, J=1.9 Hz, 1H), 8.02 (dd, J=8.8, 2.0 Hz, 1H), 7.45 (s, 1H), 5.99 (ddt, J=17.1, 10.3, 5.9 Hz, 1H), 5.41 (dq, J=17.2, 1.5 Hz, 1H), 5.32 (dq, J=10.4, 1.2 Hz, 1H), 4.72 (dt, J=5.9, 1.4 Hz, 2H). $^{13}$C NMR (126 MHz, Chloroform-d) δ 170.4, 152.6, 139.7, 131.9, 131.3, 130.3, 124.3, 121.6, 119.3, 118.7, 66.8. UV (λmax nm): 270; IR ($\nu_{max}$ cm$^{-1}$) 3320, 3082, 2982, 2950, 2827, 2651, 2537, 1703, 1681, 1229, 557; HRMS (ESI) calcd for $C_{11}H_9ClNO_4$ [M−H]$^+$: 254.0226, found: 254.0229.

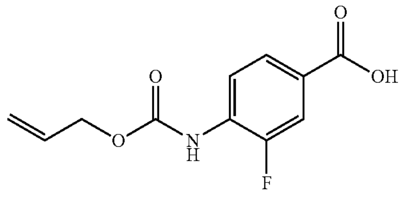 [SMILES: C=CCOC(=O)Nc1ccc(C(=O)O)cc1F]

4-(((allyloxy)carbonyl)amino)-3-fluorobenzoic acid (8c): Using the general procedure for alloc protection, compound 8c was obtained as a white solid in 89% yield. $^1$H NMR (400 MHz, Chloroform-d) δ 8.28 (t, J=8.2 Hz, 1H), 7.95-7.88 (m, 1H), 7.80 (dd, J=11.5, 2.0 Hz, 1H), 7.12 (d, J=2.7 Hz, 1H), 5.98 (ddt, J=17.0, 10.3, 5.8 Hz, 1H), 5.45-5.36 (m, 1H), 5.36-5.26 (m, 1H), 4.72 (dt, J=5.9, 1.3 Hz, 2H). $^{13}$C NMR (101 MHz, DMSO-$d_6$) δ 166.1, 166.0, 153.6, 153.3, 151.2, 132.9, 130.9, 130.8, 126.6, 126.5, 125.9, 125.8, 122.1, 117.8, 116.3, 116.1, 65.3. $^{13}$C NMR (101 MHz, DMSO-$d_6$) δ 166.1 (d, J=2.5 Hz), 153.3, 152.4 (d, J=246.3 Hz), 132.9, 130.8 (d, J=11.4 Hz), 126.6 (d, J=6.3 Hz), 125.9 (d, J=3.2 Hz), 122.1, 117.8, 116.2 (d, J=20.7 Hz), 65.3. UV (λmax nm): 264; IR ($\nu_{max}$ cm$^{-1}$) 3339, 3067, 2960, 2846, 2673, 2561, 1715, 1617, 1237, 765; HRMS (ESI) calcd for $C_{11}H_9FNO_4$ [M−H]$^+$: 238.0521, found: 238.0523.

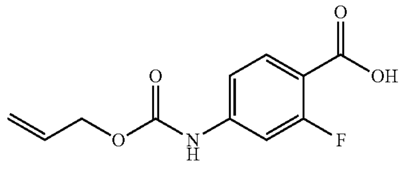 [SMILES: C=CCOC(=O)Nc1ccc(C(=O)O)c(F)c1]

4-(((allyloxy)carbonyl)amino)-2-fluorobenzoic acid (8d): Using the general procedure for alloc protection, compound 8d was obtained as a white solid in 90% yield. $^1$H NMR (400 MHz, DMSO-$d_6$) δ 12.94 (s, 1H), 10.32 (s, 1H), 7.81 (t, J=8.6 Hz, 1H), 7.44 (dd, J=13.7, 2.1 Hz, 1H), 7.29 (dd, J=8.7, 2.1 Hz, 1H), 5.99 (ddt, J=17.3, 10.7, 5.5 Hz, 1H), 5.37 (dq, J=17.3, 1.7 Hz, 1H), 5.26 (dq, J=10.5, 1.5 Hz, 1H), 4.64 (dt, J=5.5, 1.5 Hz, 2H). $^{13}$C NMR (101 MHz, DMSO-$d_6$) δ 164.6, 162.0 (d, J=255.5 Hz), 153.0, 145.0 (d, J=10.9 Hz), 133.0, 132.9 (d, J=6.5 Hz), 118.0, 113.5 (d, J=27.0 Hz), 112.3 (d, J=9.7 Hz), 105.2 (d, J=27.8 Hz), 65.2. UV (λmax nm): 264; IR ($\nu_{max}$ cm$^{-1}$) 3421, 3373, 3105, 3071, 2947, 2884, 2677, 2578, 1728, 1682, 1223, 763, 596; HRMS (ESI) calcd for $C_{11}H_9FNO_4$ [M−H]$^+$: 238.0521, found: 238.0526.

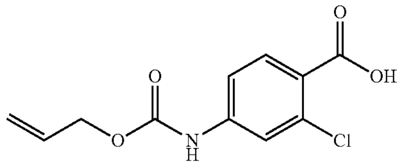 [SMILES: C=CCOC(=O)Nc1ccc(C(=O)O)c(Cl)c1]

4-(((allyloxy)carbonyl)amino)-2-chlorobenzoic acid (8e): Using the general procedure for alloc protection, compound 8a was obtained as a white solid in 83% yield. $^1$H NMR (400 MHz, DMSO-$d_6$) δ 13.07 (s, 1H), 10.24 (s, 1H), 7.82 (d, J=8.6 Hz, 1H), 7.68 (d, J=2.1 Hz, 1H), 7.46 (dd, J=8.7, 2.2 Hz, 1H), 5.99 (ddt, J=17.2, 10.8, 5.5 Hz, 1H), 5.37 (dq, J=17.2, 1.7 Hz, 1H), 5.26 (dq, J=10.5, 1.4 Hz, 1H), 4.64 (dt, J=5.5, 1.5 Hz, 2H). $^{13}$C NMR (101 MHz, DMSO-$d_6$) δ 165.9, 153.0, 143.1, 133.3, 132.9, 132.6, 123.6, 119.1, 118.0, 116.0, 65.2. UV (λmax nm): 268; IR ($\nu_{max}$ cm$^{-1}$) 3362, 3082, 2987, 2892, 2653, 2547, 1703, 1600, 1215, 658; HRMS (ESI) calcd for $C_{11}H_9ClNO_4$ [M−H]$^+$: 254.0226, found: 254.0237.

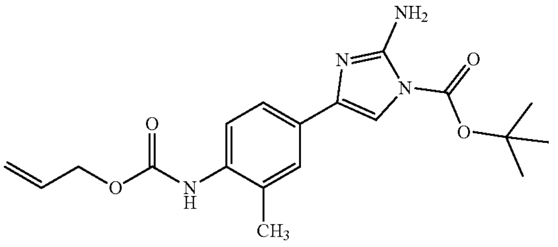 [SMILES: C=CCOC(=O)Nc1ccc(-c2cn(C(=O)OC(C)(C)C)c(N)n2)cc1C]

tert-butyl 4-(4-(((allyloxy)carbonyl)amino)-3-methylphenyl)-2-amino-1H-imidazole-1-carboxylate (9a): Using compound 8a in the general procedures for α-bromo-ketone production and Boc-guanidine cyclization, compound 9a was obtained as a blue-green solid in 27% yield. $^1$H NMR (400 MHz, Methanol-$d_4$) δ 7.55-7.33 (m, 3H), 7.15 (s, 1H), 6.00 (ddt, J=17.2, 10.7, 5.5 Hz, 1H), 5.42-5.30 (m, 1H), 5.23 (dq, J=10.4, 1.4 Hz, 1H), 4.63 (dt, J=5.5, 1.5 Hz, 2H), 2.26 (s, 3H), 1.63 (s, 9H). $^{13}$C NMR (101 MHz, DMSO-$d_6$) δ 154.1, 150.4, 149.0, 136.7, 135.1, 133.5, 131.3, 130.0, 126.6, 124.5, 122.5, 117.4, 105.7, 84.6, 64.7, 27.6, 17.9. UV (λmax nm): 226; IR ($\nu_{max}$ cm$^{-1}$) 3449, 3292, 2979, 2928, 1730, 1353, 1116; HRMS (ESI) calcd for $C_{19}H2_5N_4O_4$ [M+H]$^+$: 373.1870, found: 373.1879.

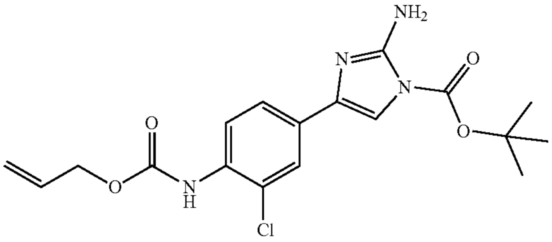 [SMILES: C=CCOC(=O)Nc1ccc(-c2cn(C(=O)OC(C)(C)C)c(N)n2)cc1Cl]

tert-butyl 4-(4-(((allyloxy)carbonyl)amino)-3-chlorophenyl)-2-amino-1H-imidazole-1-carboxylate (9b): Using compound 8b in the general procedures for α-bromo-ketone production and Boc-guanidine cyclization, compound 9b was obtained as an off-white solid in 54% yield. $^{1}$H NMR (400 MHz, Chloroform-d) δ 8.15 (d, J=8.7 Hz, 1H), 7.73 (d, J=2.0 Hz, 1H), 7.56 (dd, J=8.7, 2.0 Hz, 1H), 7.20 (s, 1H), 7.06 (s, 1H), 5.99 (ddt, J=17.2, 10.4, 5.8 Hz, 1H), 5.64 (s, 2H), 5.39 (dq, J=17.1, 1.5 Hz, 1H), 5.29 (dq, J=10.5, 1.3 Hz, 1H), 4.69 (dt, J=5.8, 1.4 Hz, 2H), 1.62 (s, 9H). $^{13}$C NMR (101 MHz, DMSO-$d_6$) δ 153.9, 150.5, 148.9, 135.2, 133.3, 133.2, 131.8, 127.6, 126.2, 125.3, 123.6, 117.5, 107.1, 84.8, 65.0, 27.6. UV (λmax nm): 316; IR ($\nu_{max}$ cm$^{-1}$) 3388, 3279, 3104, 2975, 2932, 1734, 1158; HRMS (ESI) calcd for $C_{18}H_{22}ClN_4O_4$[M+H]$^+$: 393.1324, found: 393.1314.

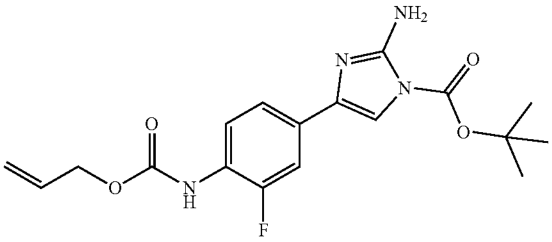 [SMILES: C=CCOC(=O)Nc1ccc(-c2cn(C(=O)OC(C)(C)C)c(N)n2)cc1F]

tert-butyl 4-(4-(((allyloxy)carbonyl)amino)-3-fluorophenyl)-2-amino-1H-imidazole-1-carboxylate (9c): Using compound 8c in the general procedures for α-bromo-ketone production and Boc-guanidine cyclization, compound 9c was obtained as an off-white solid in 51o % yield. $^{1}$H NMR (400 MHz, DMSO-$d_6$) δ 9.40 (s, 1H), 7.63-7.49 (m, 3H), 7.42 (s, 1H), 6.63 (s, 2H), 5.97 (ddt, J=17.3, 10.6, 5.4 Hz, 1H), 5.36 (dq, J=17.2, 1.7 Hz, 1H), 5.23 (dq, J=10.5, 1.5 Hz, 1H), 4.60 (dt, J=5.4, 1.5 Hz, 2H), 1.58 (s, 9H). $^{13}$C NMR (101 MHz, DMSO-$d_6$) δ 156.0, 153.6, 151.8 (d, J=266.1 Hz), 149.3, 136.1 (d, J=2.5 Hz), 133.2, 131.5 (d, J=7.1 Hz), 124.9 (d, J=12.0 Hz), 120.9 (d, J=2.9 Hz), 118.0, 112.0 (d, J=21.0 Hz), 107.3, 85.2, 65.4, 28.0. UV (λmax nm): 308; IR ($\nu_{max}$ cm$^{-1}$) 3417, 3344, 2975, 2936, 1736, 1596, 1212, 525; HRMS (ESI) calcd for $C_{18}H_{22}FN_4O_4$[M+H]$^+$: 377.1620, found: 377.1629.

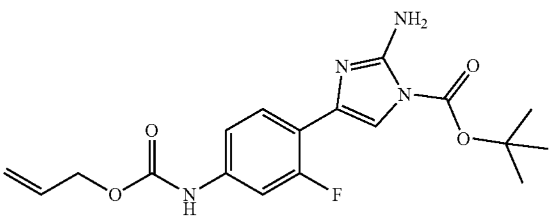 [SMILES: C=CCOC(=O)Nc1ccc(-c2cn(C(=O)OC(C)(C)C)c(N)n2)c(F)c1]

tert-butyl 4-(4-(((allyloxy)carbonyl)amino)-2-fluorophenyl)-2-amino-1H-imidazole-1-carboxylate (9d): Using compound 8d in the general procedures for α-bromo-ketone production and Boc-guanidine cyclization, compound 9d was obtained as a white solid in 54% yield. $^{1}$H NMR (400 MHz, Chloroform-d) δ 7.87 (t, J=8.5 Hz, 1H), 7.47 (d, J=13.4 Hz, 1H), 7.21 (d, J=3.8 Hz, 1H), 6.97 (dd, J=8.5, 2.2 Hz, 1H), 6.71 (s, 1H), 5.97 (ddt, J=17.1, 10.3, 5.8 Hz, 1H), 5.67 (s, 2H), 5.37 (dq, J=17.2, 1.5 Hz, 1H), 5.28 (dq, J=10.4, 1.3 Hz, 1H), 4.68 (dt, J=5.8, 1.4 Hz, 2H), 1.62 (s, 9H). $^{13}$C NMR (101 MHz, Chloroform-d) δ 160.2 (d, J=248.3 Hz), 153.1, 150.0, 149.5, 137.9 (d, J=11.5 Hz), 132.4, 131.0 (d, J=2.5 Hz), 128.2 (d, J=5.4 Hz), 118.6, 116.2 (d, J=13.3 Hz), 114.3-113.9 (m), 109.9 (d, J=15.4 Hz), 106.2 (d, J=27.0 Hz), 85.6, 66.2, 28.1. UV (λmax nm): 302; IR ($\nu_{max}$ cm$^{-1}$) 341, 3340, 3119, 2979, 1733, 1595, 1396, 1205, 738; HRMS (ESI) calcd for $C_{18}H_{22}FN_4O_4$[M+H]$^+$: 377.1620, found: 377.1631.

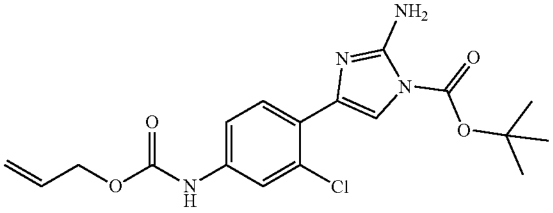 [SMILES: C=CCOC(=O)Nc1ccc(-c2cn(C(=O)OC(C)(C)C)c(N)n2)c(Cl)c1]

tert-butyl 4-(4-(((allyloxy)carbonyl)amino)-2-chlorophenyl)-2-amino-1H-imidazole-1-carboxylate (9e): Using compound 8e in the general procedures for α-bromo-ketone production and Boc-guanidine cyclization, compound 9e was obtained as a white solid in 53% yield. $^{1}$H NMR (400 MHz, Chloroform-d) δ 7.86 (d, J=8.6 Hz, 1H), 7.61 (s, 1H), 7.44 (s, 1H), 7.15 (d, J=8.4 Hz, 1H), 7.00 (s, 1H), 5.96 (ddt, J=17.3, 10.4, 5.7 Hz, 1H), 5.78 (s, 2H), 5.37 (dq, J=17.2, 1.5 Hz, 1H), 5.27 (dq, J=10.4, 1.3 Hz, 1H), 4.67 (dt, J=5.8, 1.4 Hz, 2H), 1.62 (s, 9H). $^{13}$C NMR (101 MHz, DMSO-$d_6$) δ 153.1, 149.5, 148.7, 138.7, 133.1, 133.1, 130.0, 129.7, 125.3, 119.0, 117.9, 116.7, 109.0, 85.0, 64.9, 27.5. UV (λmax nm): 228; IR ($\nu_{max}$ cm$^{-1}$) 3436, 3294, 3223, 3185, 2987, 2934, 1735, 1705, 1149, 736; HRMS (ESI) calcd for $C_{18}H_{22}ClN_4O_4$[M+H]$^+$: 393.1324, found: 393.1312.

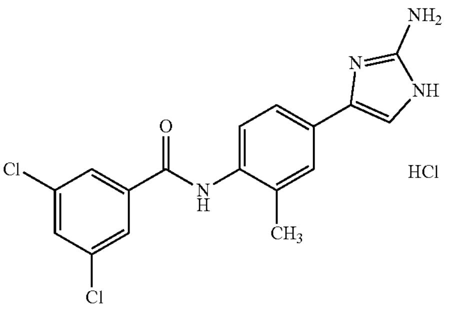 [SMILES: Cc1cc(-c2c[nH]c(N)n2)ccc1NC(=O)c1cc(Cl)cc(Cl)c1 ; Cl]

N-(4-(2-amino-1H-imidazol-4-yl)-2-methylphenyl)-3,5-dichlorobenzamide hydrochloride (10a): Using compound 9a in the general procedures for alloc deprotection, amide formation, and Boc deprotection, compound 10a was obtained as a white solid in 89% yield. $^{1}$H NMR (400 MHz, DMSO-$d_6$) δ 12.73 (s, 1H), 12.06 (s, 1H), 10.19 (s, 1H), 8.00 (d, J=1.9 Hz, 2H), 7.90 (t, J=1.9 Hz, 1H), 7.60 (d, J=2.2 Hz, 1H), 7.55-7.44 (m, 3H), 7.44-7.37 (m, 2H), 2.26 (s, 3H); $^{13}$C NMR (101 MHz, DMSO-$d_6$) δ 162.8, 147.7, 137.6, 135.6, 134.4, 134.3, 131.0, 126.9, 126.6, 126.2, 126.1, 125.7, 122.0, 109.4, 18.0. UV (λmax nm): 226; IR ($\nu_{max}$ cm$^{-1}$) 3404, 3258, 3121, 3080, 3062, 2919, 2773, 2743, 1680, 1566, 1243, 780; HRMS (ESI) calcd for $C_{17}H_{15}C_{12}N_4O$ [M+H]$^+$: 361.0617, found: 361.0628.

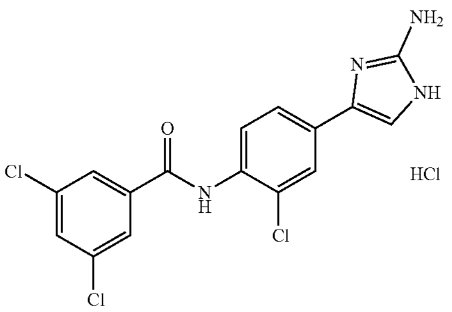 [SMILES: Nc1nc(-c2ccc(NC(=O)c3cc(Cl)cc(Cl)c3)c(Cl)c2)c[nH]1 ; Cl]

N-(4-(2-amino-1H-imidazol-4-yl)-2-chlorophenyl)-3,5-dichlorobenzamide hydrochloride (10b): Using compound 9b in the general procedures for alloc deprotection, amide formation, and Boc deprotection, compound 10b was obtained as a white solid in 93% yield. $^1$H NMR (400 MHz, Methanol-$d_4$) δ 7.94 (d, J=1.8 Hz, 2H), 7.83-7.78 (m, 2H), 7.74 (t, J=1.9 Hz, 1H), 7.59 (dd, J=8.4, 2.1 Hz, 1H), 7.28 (s, 1H). $^{13}$C NMR (101 MHz, DMSO-$d_6$) δ 162.9, 147.9, 142.0, 137.0, 134.5, 133.7, 131.4, 130.2, 128.9, 127.5, 126.6, 125.0, 123.2, 110.8. UV (λmax nm): 224; IR ($\nu_{max}$ cm$^{-1}$) 3289, 3118, 3039, 3004, 1691, 1644, 720; HRMS (ESI) calcd for $C_{16}H_{12}C_{13}N_4O$ [M+H]$^+$: 381.0071, found: 381.0080.

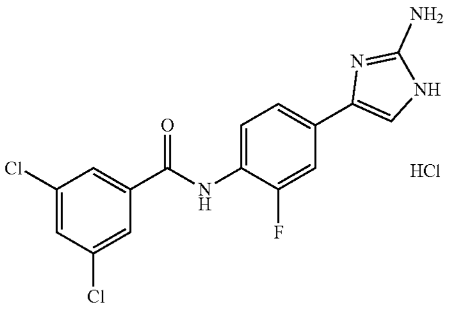 [SMILES: Nc1nc(-c2ccc(NC(=O)c3cc(Cl)cc(Cl)c3)c(F)c2)c[nH]1 ; Cl]

N-(4-(2-amino-1H-imidazol-4-yl)-2-fluorophenyl)-3,5-dichlorobenzamide hydrochloride (10c): Using compound 9c in the general procedures for alloc deprotection, amide formation, and Boc deprotection, compound 10c was obtained as a white solid in 98% yield. $^1$H NMR (500 MHz, DMSO-$d_6$) δ 12.95 (s, 1H), 12.19 (s, 1H), 10.50 (s, 1H), 8.00 (d, J=1.9 Hz, 2H), 7.91 (t, J=1.9 Hz, 1H), 7.73-7.66 (m, 2H), 7.57 (s, 2H), 7.54 (dd, J=8.3, 2.0 Hz, 1H), 7.50 (s, 1H). $^{13}$C NMR (126 MHz, DMSO-$d_6$) δ 162.9, 155.6 (d, J=247.1 Hz), 147.8, 137.0, 134.4, 131.3, 127.2 (d, J=2.5 Hz), 126.9 (d, J=8.6 Hz), 126.7, 125.2 (d, J=2.6 Hz), 124.6 (d, J=12.6 Hz), 120.1 (d, J=3.1 Hz), 111.8 (d, J=22.6 Hz), 110.6. UV (λmax nm): 320; IR ($\nu_{max}$ cm$^{-1}$) 3421, 3355, 3293, 3211, 3153, 3076, 3043, 1663, 1519, 703; HRMS (ESI) calcd for $C_{16}H_{12}Cl_2FN_4O$ [M+H]$^+$: 365.0367, found: 365.0359.

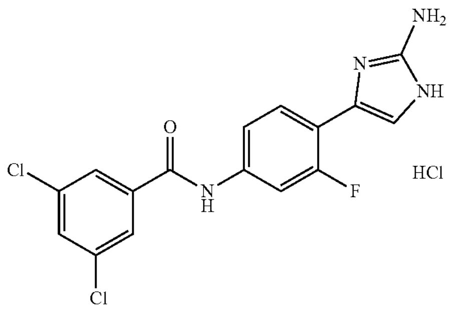 [SMILES: Nc1nc(-c2ccc(NC(=O)c3cc(Cl)cc(Cl)c3)cc2F)c[nH]1 ; Cl]

N-(4-(2-amino-1H-imidazol-4-yl)-3-fluorophenyl)-3,5-dichlorobenzamide hydrochloride (10d): Using compound 9d in the general procedures for alloc deprotection, amide formation, and Boc deprotection, compound 10d was obtained as a tan solid in 98% yield. $^1$H NMR (400 MHz, DMSO-$d_6$) δ 12.57 (s, 1H), 12.17 (s, 1H), 10.74 (s, 1H), 7.99 (d, J=1.9 Hz, 2H), 7.92 (t, J=1.9 Hz, 1H), 7.87 (dd, J=13.8, 2.0 Hz, 1H), 7.72 (t, J=8.6 Hz, 1H), 7.65 (dd, J=8.7, 2.0 Hz, 1H), 7.47 (s, 2H), 7.21 (d, J=2.3 Hz, 1H). $^{13}$C NMR (126 MHz, DMSO-$d_6$) δ 163.1, 158.0 (d, J=246.3 Hz), 147.6, 139.7 (d, J=11.3 Hz), 137.5, 134.4, 131.3, 126.7 (d, J=18.1 Hz), 126.6, 120.4 (d, J=2.1 Hz), 116.3 (d, J=2.9 Hz), 111.8 (d, J=11.0 Hz), 111.2 (d, J=12.9 Hz), 107.7 (d, J=26.7 Hz). UV (λmax nm): 322; IR ($\nu_{max}$ cm$^{-1}$) 3443, 3237, 3181, 3065, 1687, 797, 660; HRMS (ESI) calcd for $C_{16}H_{12}C_{12}FN_4O$ [M+H]$^+$: 365.0367, found: 365.0378.

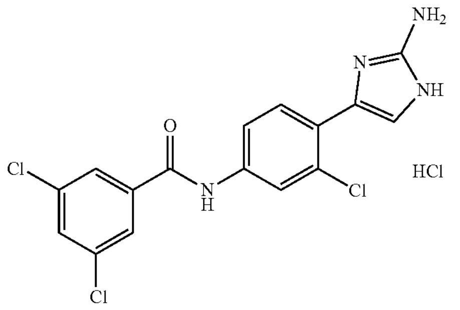 [SMILES: Nc1nc(-c2ccc(NC(=O)c3cc(Cl)cc(Cl)c3)cc2Cl)c[nH]1 ; Cl]

N-(4-(2-amino-1H-imidazol-4-yl)-3-chlorophenyl)-3,5-dichlorobenzamide hydrochloride (10e): Using compound 9e in the general procedures for alloc deprotection, amide formation, and Boc deprotection, compound 10e was obtained as a white solid in 94% yield. $^1$H NMR (400 MHz, Methanol-$d_4$) δ 8.07 (d, J=2.1 Hz, 1H), 7.93 (d, J=1.9 Hz, 2H), 7.79 (dd, J=8.6, 2.2 Hz, 1H), 7.72 (t, J=1.9 Hz, 1H), 7.54 (d, J=8.6 Hz, 1H), 7.16 (s, 1H). $^{13}$C NMR (101 MHz, Methanol-$d_4$) δ 165.7, 148.9, 141.3, 139.0, 136.6, 133.3, 132.7, 130.9, 127.5, 125.2, 123.4, 123.1, 120.4, 113.5. UV (λmax nm): 204; IR ($\nu_{max}$ cm$^{-1}$) 3474, 3238, 3204, 3135, 1682, 1564, 663; HRMS (ESI) calcd for $C_{16}H_{12}Cl_3N_4O$ [M+H]$^+$: 381.0071, found: 381.0082.

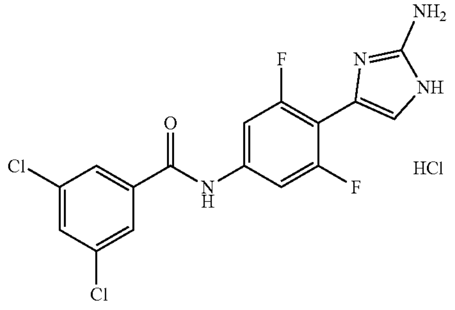 [SMILES: Nc1nc(-c2c(F)cc(NC(=O)c3cc(Cl)cc(Cl)c3)cc2F)c[nH]1 ; Cl]

N-(4-(2-amino-1H-imidazol-4-yl)-3,5-difluorophenyl)-3,5-dichlorobenzamide hydrochloride (13): Using compound 11 in the general procedures for amide formation, saponification, α-bromo-ketone production, Boc-guanidine cyclization, and Boc deprotection, compound 13 was obtained as a white solid in 92% yield. $^{1}$H NMR (400 MHz, DMSO-$d_6$) δ 12.36 (s, 2H), 11.08 (s, 1H), 8.04 (d, J=1.9 Hz, 2H), 7.92 (t, J=1.9 Hz, 1H), 7.75 (d, J=11.1 Hz, 2H), 7.57 (s, 2H), 7.21 (s, 1H). $^{13}$C NMR (101 MHz, DMSO-$d_6$) δ 163.4, 158.6 (dd, J=246.5, 9.2 Hz), 147.6, 140.4 (t, J=14.6 Hz), 137.1, 134.5, 131.5, 126.7, 113.9, 103.8 (d, J=8.3 Hz), 103.5 (d, J=8.0 Hz), 100.9 (t, J=17.9 Hz). UV (λmax nm): 322; IR ($\nu_{max}$ $cm^{-1}$) 3306, 3203, 3150, 3070, 1687, 801, 669; HRMS (ESI) calcd for $C_{16}H_{11}Cl_2F_2N_4O$ $[M+H]^+$: 383.0272, found: 383.0272.

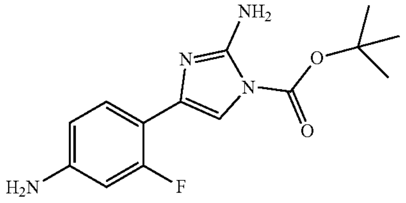 [SMILES: CC(C)(C)OC(=O)n1cc(-c2ccc(N)cc2F)nc1N]

tert-butyl 2-amino-4-(4-amino-2-fluorophenyl)-1H-imidazole-1-carboxylate (14): Using compound 9d in the general procedures for alloc deprotection, compound 14 was obtained as an orange solid in 98% yield. $^{1}$H NMR (400 MHz, Methanol-$d_4$) δ 7.53 (t, J=8.6 Hz, 1H), 6.99 (d, J=3.9 Hz, 1H), 6.50 (dd, J=8.4, 2.2 Hz, 1H), 6.43 (dd, J=13.7, 2.2 Hz, 1H), 1.62 (s, 9H). $^{13}$C NMR (101 MHz, Methanol-$d_4$) δ 163.6 (d, J=245.8 Hz), 152.1, 150.7, 150.5 (d, J=11.6 Hz), 132.9 (d, J=2.2 Hz), 129.3 (d, J=5.8 Hz), 111.8 (d, J=39.0 Hz), 110.7 (d, J=13.5 Hz), 108.6 (d, J=15.1 Hz), 102.6 (d, J=25.2 Hz), 86.4, 28.1. UV (λmax nm): 322; IR ($\nu_{max}$ $cm^{-1}$) 3457, 3346, 3209, 2927, 2873, 1732, 1618, 1119, 695; HRMS (ESI) calcd for $C_{14}H_{18}FN_4O_2$$[M+H]^+$: 293.1408, found: 293.1413.

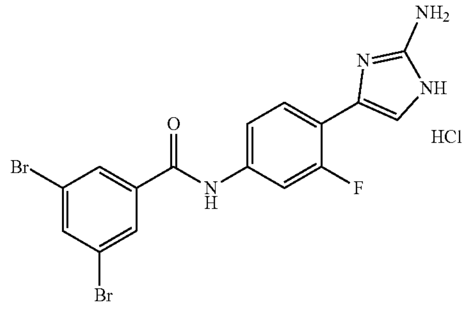 [SMILES: Nc1nc(-c2ccc(NC(=O)c3cc(Br)cc(Br)c3)cc2F)c[nH]1 ; Cl]

N-(4-(2-amino-1H-imidazol-4-yl)-3-fluorophenyl)-3,5-dibromobenzamide hydrochloride (15a): Using compound 14 in the general procedures for amide formation and Boc deprotection, compound 15a was obtained as a tan solid in 83% yield. $^{1}$H NMR (400 MHz, DMSO-$d_6$) δ 12.87 (s, 1H), 12.27 (s, 1H), 10.82 (s, 1H), 8.17 (d, J=1.7 Hz, 2H), 8.12 (t, J=1.7 Hz, 1H), 7.89 (dd, J=13.8, 2.0 Hz, 1H), 7.75 (t, J=8.6 Hz, 1H), 7.67 (dd, J=8.7, 2.0 Hz, 1H), 7.51 (s, 2H), 7.19 (d, J=2.3 Hz, 1H). $^{13}$C NMR (101 MHz, DMSO-$d_6$) δ 162.9, 158.0 (d, J=246.6 Hz), 147.6, 139.7 (d, J=11.2 Hz), 137.9, 136.6, 129.8, 126.7 (d, J=4.2 Hz), 122.7, 120.3 (d, J=1.9 Hz), 116.3 (d, J=2.8 Hz), 111.8 (d, J=11.0 Hz), 111.2 (d, J=12.9 Hz), 107.7 (d, J=26.5 Hz). UV (λmax nm): 210; IR ($\nu_{max}$ $cm^{-1}$) 3362, 3246, 3172, 3149, 3070, 3018, 1687, 1660, 1517, 1140, 659; HRMS (ESI) calcd for $C_{16}H_{12}Br_2FN_4O$ $[M+H]^+$: 452.9356, found: 452.9338.

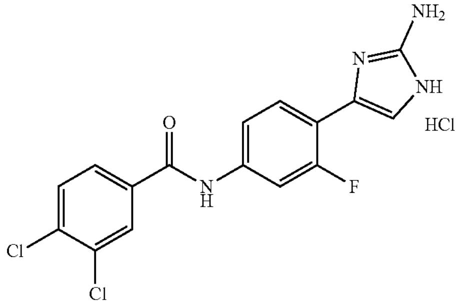 [SMILES: Nc1nc(-c2ccc(NC(=O)c3ccc(Cl)c(Cl)c3)cc2F)c[nH]1 ; Cl]

N-(4-(2-amino-1H-imidazol-4-yl)-3-fluorophenyl)-3,4-dichlorobenzamide hydrochloride (15b): Using compound 14 in the general procedures for amide formation and Boc deprotection, compound 15b was obtained as a white solid in 96% yield. $^{1}$H NMR (400 MHz, DMSO-$d_6$) δ 12.91 (s, 1H), 12.28 (s, 1H), 10.85 (s, 1H), 8.27 (d, J=2.1 Hz, 1H), 7.98 (dd, J=8.4, 2.1 Hz, 1H), 7.92 (dd, J=13.9, 2.0 Hz, 1H), 7.84 (d, J=8.4 Hz, 1H), 7.75 (t, J=8.6 Hz, 1H), 7.69 (dd, J=8.7, 2.0 Hz, 1H), 7.52 (s, 2H), 7.19 (d, J=2.3 Hz, 1H). $^{13}$C NMR (101 MHz, DMSO-$d_6$) δ 163.5, 158.0 (d, J=246.3 Hz), 147.6, 139.9 (d, J=11.4 Hz), 134.7 (d, J=15.8 Hz), 131.4, 130.9, 129.8, 128.2, 126.7, 126.7, 120.3, 116.3 (d, J=2.6 Hz), 111.7 (d, J=11.5 Hz), 111.1 (d, J=13.1 Hz), 107.6 (d, J=26.7 Hz). UV (λmax nm): 322; IR ($\nu_{max}$ $cm^{-1}$) 3464, 3324, 3273, 3132, 3064, 1682, 780, 677; HRMS (ESI) calcd for $C_{16}H_{12}Cl_2FN_4O$ $[M+H]^+$: 365.0367, found: 365.0369.

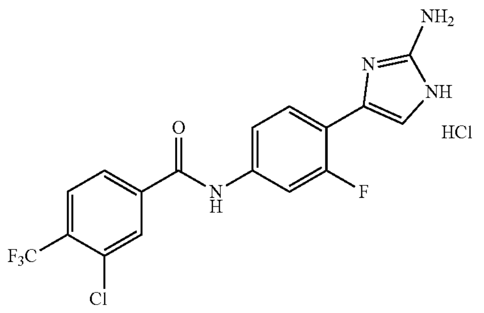 [SMILES: Nc1nc(-c2ccc(NC(=O)c3ccc(C(F)(F)F)c(Cl)c3)cc2F)c[nH]1 ; Cl]

N-(4-(2-amino-1H-imidazol-4-yl)-3-fluorophenyl)-3-chloro-4-(trifluoromethyl)benzamide hydrochloride (17a): Using compound 16 in the general procedures for amide formation using EDC coupling, saponification, α-bromo-ketone production, Boc-guanidine cyclization, and Boc deprotection, compound 17a was obtained as a white solid in 90% yield. $^{1}$H NMR (400 MHz, DMSO-$d_6$) δ 12.57 (s, 1H), 10.86 (s, 1H), 8.28 (s, 1H), 8.13-8.01 (m, 2H), 7.89 (dd, J=13.6, 1.5 Hz, 1H), 7.73 (t, J=8.6 Hz, 1H), 7.66 (dd, J=8.6, 1.9 Hz, 1H), 7.47 (s, 2H), 7.22 (d, J=2.2 Hz, 1H). $^{13}$C NMR (126 MHz, Methanol-$d_4$) δ 165.7, 160.3 (d, J=247.0 Hz), 149.1, 141.4 (d, J=11.4 Hz), 140.9, 133.5 (d, J=2.0 Hz), 132.2-131.4 (m), 129.2 (q, J=5.2 Hz), 127.7 (d, J=4.0 Hz), 127.6, 125.1, 122.9 (d, J=19.0 Hz), 122.8, 117.7 (d, J=3.0 Hz), 112.8 (d, J=13.2 Hz), 112.6 (d, J=10.7 Hz), 109.3 (d, J=27.2 Hz). UV (λmax nm): 306; HRMS (ESI) calcd for $C_{17}H_{12}ClF_4N_4O$ $[M+H]^+$: 399.0630, found: 399.0634.

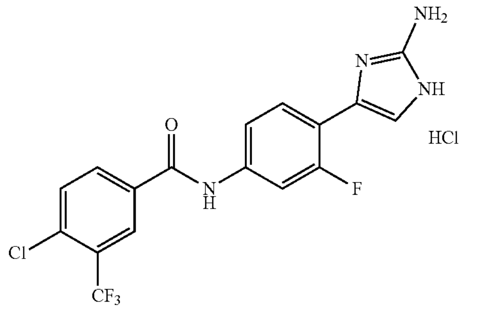 [SMILES: Nc1nc(-c2ccc(NC(=O)c3ccc(Cl)c(C(F)(F)F)c3)cc2F)c[nH]1 ; Cl]

N-(4-(2-amino-1H-imidazol-4-yl)-3-fluorophenyl)-4-chloro-3-(trifluoromethyl)benzamide hydrochloride (17b): Using compound 16 in the general procedures for amide formation using EDC coupling, saponification, α-bromo-ketone production, Boc-guanidine cyclization, and Boc deprotection, compound 17b was obtained as a white solid in 35% yield. $^{1}$H NMR (500 MHz, DMSO-$d_6$) δ 12.88 (s, 1H), 12.27 (s, 1H), 10.98 (s, 1H), 8.41 (d, J=2.2 Hz, 1H), 8.31 (dd, J=8.4, 2.2 Hz, 1H), 7.97-7.89 (m, 2H), 7.76 (t, J=8.7 Hz, 1H), 7.69 (dd, J=8.7, 2.0 Hz, 1H), 7.52 (s, 2H), 7.20 (d, J=2.3 Hz, 1H). $^{13}$C NMR (126 MHz, DMSO-$d_6$) δ 163.5, 158.0 (d, J=246.5 Hz), 147.6, 139.8 (d, J=11.4 Hz), 134.3 (d, J=2.0 Hz), 133.6 (d, J=5.1 Hz), 132.0, 127.3 (q, J=5.2 Hz), 127.0-126.6 (m), 123.7, 121.6, 120.3 (d, J=1.8 Hz), 116.4 (d, J=2.9 Hz), 111.8 (d, J=11.3 Hz), 111.2 (d, J=13.2 Hz), 107.7 (d, J=26.7 Hz). UV (λmax nm): 306; HRMS (ESI) calcd for $C_{17}H_{12}ClF_4N_4O$ $[M+H]^+$: 399.0630, found: 399.0633.

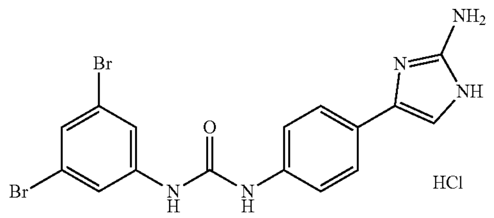 [SMILES: Nc1nc(-c2ccc(NC(=O)Nc3cc(Br)cc(Br)c3)cc2)c[nH]1 ; Cl]

1-(4-(2-amino-1H-imidazol-4-yl)phenyl)-3-(3,5-dibromophenyl)urea hydrochloride (20a): To a solution of compound 3 (1 eq, 0.21 mmol) dissolved in DCM (12 mL) was added sodium carbonate (1.6 eq, 0.34 mmol) dissolved in dI water (12 mL). After the solution was stirred for 5 min, triphosgene (0.33 eq, 0.07 mmol) dissolved in DCM (2 mL) was added to the flask. After the solution was stirred for 0.5 h, 3,5-dibromoaniline (1.3 eq, 0.27 mmol) dissolved in DCM (2 mL) was added dropwise and allowed to stir for an additional 2 h. The mixture was then separated, and the aqueous layer was washed twice with DCM. The organics were combined, dried with $MgSO_4$, and concentrated under reduced pressure. The resulting solid was purified using flash chromatography (0-33% EtOAc in hexanes). The collected urea product was used in the general procedure for Boc deprotection to obtain compound 20a as a tan solid in 87% yield. $^{1}$H NMR (400 MHz, Methanol-$d_4$) δ 7.69 (d, J=1.7 Hz, 2H), 7.58-7.47 (m, 4H), 7.34 (t, J=1.7 Hz, 1H), 7.08 (s, 1H). $^{13}$C NMR (101 MHz, Methanol-$d_4$) δ 154.3, 149.1, 143.3, 140.6, 128.9, 128.5, 126.2, 123.8, 123.4, 121.2, 120.5, 109.0. UV (λmax nm): 228; IR ($\nu_{max}$ $cm^{-1}$) 3272, 3258, 3133, 3043, 1672, 1511, 664; HRMS (ESI) calcd for $C_{16}H_{14}Br_2N_5O$ $[M+H]^+$: 449.9560, found: 449.9542.

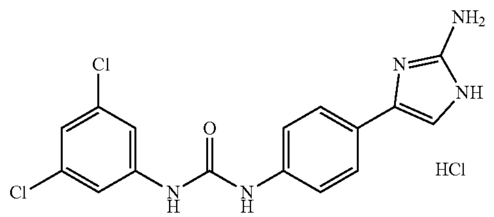 [SMILES: Nc1nc(-c2ccc(NC(=O)Nc3cc(Cl)cc(Cl)c3)cc2)c[nH]1 ; Cl]

1-(4-(2-amino-1H-imidazol-4-yl)phenyl)-3-(3,5-dichlorophenyl)urea hydrochloride (20b): The above compound was synthesized in a similar manner to compound 20a, followed by using the general procedure for Boc deprotection to obtain 20b as a tan solid in 99% yield. $^{1}$H NMR (400 MHz, Methanol-$d_4$) δ 7.58-7.50 (m, 4H), 7.50 (d, J=1.6 Hz, 2H), 7.08 (s, 1H), 7.07 (t, J=1.9 Hz, 1H). $^{13}$C NMR (101 MHz, DMSO-$d_6$) δ 152.3, 147.5, 142.3, 139.1, 134.2, 126.5, 125.0, 121.6, 120.8, 118.3, 115.9, 108.3. UV (λmax nm): 308; IR ($\nu_{max}$ $cm^{-1}$) 3258, 3150, 3039, 1674, 1513, 665; HRMS (ESI) calcd for $C_{16}H_{14}C_{12}N_5O$ $[M+H]^+$: 362.0570, found: 362.0574.

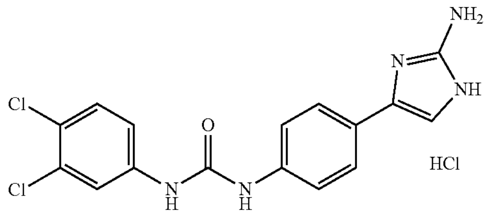 [SMILES: Nc1nc(-c2ccc(NC(=O)Nc3ccc(Cl)c(Cl)c3)cc2)c[nH]1 ; Cl]

1-(4-(2-amino-1H-imidazol-4-yl)phenyl)-3-(3,4-dichlorophenyl)urea hydrochloride (20c): The above compound was synthesized in a similar manner to compound 20a, followed by using the general procedure for Boc deprotection to obtain 20c as a white solid in 99% yield. $^{1}H$ NMR (400 MHz, Methanol-$d_4$) δ 7.81 (d, J=2.5 Hz, 1H), 7.55 (d, J=8.9 Hz, 2H), 7.50 (d, J=8.8 Hz, 2H), 7.41 (d, J=8.8 Hz, 1H), 7.30 (dd, J=8.8, 2.5 Hz, 1H), 7.07 (s, 1H). $^{13}C$ NMR (126 MHz, Methanol-$d_4$) δ 154.5, 149.1, 140.7, 140.6, 133.3, 131.5, 128.9, 126.2, 126.2, 123.2, 121.3, 120.5, 119.6, 108.9. UV (max nm): 332; (ESI) calcd for $C_{16}H_{14}C_{12}N_5O$ $[M+H]^+$: 362.0570, found: 362.0573.

Example 3. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |

-continued

| (x) Topical Cream 1 | wt. % |
|---|---|
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula III:

(III)

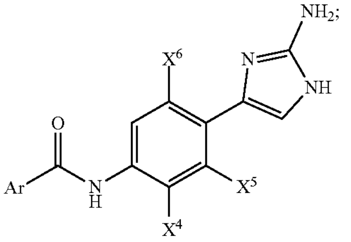

wherein $X^4$ and $X^6$ are H, and $X^5$ is F; and Ar is:

(15a)

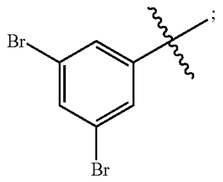

(15b)

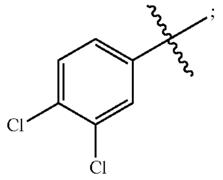

(17a)

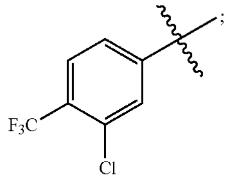

(17b)

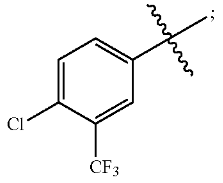

or a salt thereof.

2. A compound wherein the compound is:

10d

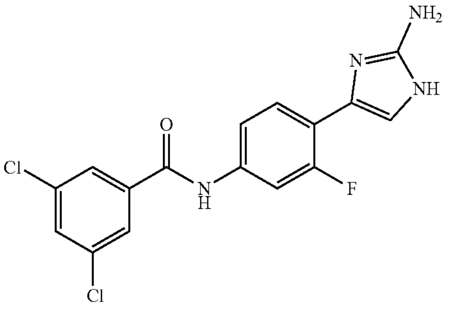

or

15b

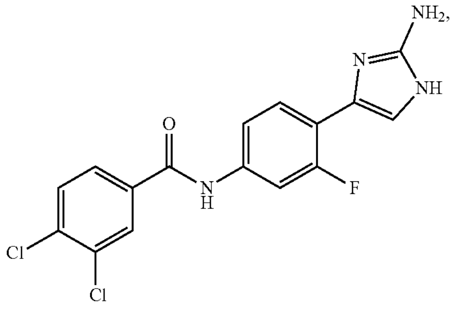

or a salt thereof.

3. A composition comprising a compound of claim 2, an antibiotic, and a pharmaceutically acceptable buffer, carrier, diluent, or excipient.

* * * * *